(12) United States Patent
David

(10) Patent No.: US 12,245,994 B2
(45) Date of Patent: *Mar. 11, 2025

(54) USE OF ATOVAQUONE AND PROGUANIL FOR TREATMENT OF GASTROINTESTINAL DISEASES AND INFLAMMATION

(71) Applicant: Elevaid Therapeutics, Inc., Chandler, AZ (US)

(72) Inventor: Joseph David, Chandler, AZ (US)

(73) Assignee: Elevaid Therapeutics, Inc., Chandler, AZ (US)

( * ) Notice: Subject to any disclaimer, the term of this patent is extended or adjusted under 35 U.S.C. 154(b) by 169 days.

This patent is subject to a terminal disclaimer.

(21) Appl. No.: 18/073,885

(22) Filed: Dec. 2, 2022

(65) Prior Publication Data

US 2023/0201135 A1    Jun. 29, 2023

Related U.S. Application Data

(63) Continuation of application No. PCT/US2021/036207, filed on Jun. 7, 2021.

(60) Provisional application No. 63/036,308, filed on Jun. 8, 2020.

(51) Int. Cl.
| | |
|---|---|
| *A61K 31/122* | (2006.01) |
| *A61K 31/155* | (2006.01) |
| *A61K 45/06* | (2006.01) |
| *A61P 1/00* | (2006.01) |

(52) U.S. Cl.
CPC ............ *A61K 31/122* (2013.01); *A61K 45/06* (2013.01); *A61P 1/00* (2018.01); *A61K 31/155* (2013.01)

(58) Field of Classification Search
CPC ................. A61K 31/122; A61P 1/00
See application file for complete search history.

(56) References Cited

U.S. PATENT DOCUMENTS

| 6,051,604 A | 4/2000 | Fitzgerald |
| 9,492,406 B2 | 11/2016 | Kumar et al. |
| 2019/0381055 A1 | 12/2019 | Cong |

FOREIGN PATENT DOCUMENTS

WO    2017065495 A2    4/2017

OTHER PUBLICATIONS

Camus, D. et al., "Atovaquone-Proguanil versus Chloroquine-Proguanil for Malaria Prophylaxis in Nonimmune Pediatric Travelers: Results of an International, Randomized, Open-Label Study," Clinical Infectious Diseases (2004); 38(12): pp. 1716-1723.
Terziroli Beretta-Piccoli Benedetta et al: "Atovaquone/proguanil-induced autoimmune-like hepatitis", Hepatology Communications, vol. 1, No. 4, May 8, 2017 (May 8, 2017), pp. 293-298, XP093188876, ISSN: 2471-254X, DOI: 10.1002/hep4.1039 Retrieved from the Internet: URL:https://api.wiley.com/onlinelibrary/td m/v1/articles/10.1002%2Fhep4.1039>.
Helieh s. oz et al: "Atovaquone ameliorate gastrointestinal Toxoplasmosis complications in a pregnancy model", Medical Science Monitor, vol. 18, No. 9, Jan. 1, 2012 (Jan. 1, 2012), pp. BR337-BR345, XP055767925, PL ISSN: 1234-1010, DOI: 10.12659/MSM.883342.
Anwar-Bruni Dominique M. et al: "Atovaquone is effective treatment for the symptoms of gastrointestinal microsporidiosis in HIV-1-infected patients", AIDS, Jun. 30, 1996 (Jun. 30, 1996), pp. 619-623, XP093188713, https://journals.lww.com/aidsonline/abstract/1996/06000/atovaquone_is_effective_treatment_for_the_symptoms.7.aspx Retrieved from the Internet: URL:https://pubmed.ncbi.nlm.nih.gov/878081 6/.
Fiorillo et al: "Repurposing atovaquone: targeting mitochondrial complex III and OXPHOS to eradicate cancer stem cells", Apr. 30, 2016, vol. 7, No. 23, Apr. 30, 2016 (Apr. 30, 2016) , pp. 34084-34099, XP002790018, DOI: 10.18632/ONCOTARGET.9122.
Subramanian V et al: 11 Primary cytomegalovirus infectious colitis complicating Crohn's disease successfully treated with oral valganciclovir, Journal of Crohn's and Colitis, Elsevier BV, NL, vol. 4, No. 2, Jun. 1, 2010 (Jun. 1, 2010), pp. 199-202, XP027047689, IS SN: 18 7 3 -9 9 4 6.
EESR issued on Aug. 6, 2024 in EP21823007.6.

*Primary Examiner* — Kevin E Weddington
(74) *Attorney, Agent, or Firm* — Fox Rothschild LLP

(57) ABSTRACT

The disclosure relates to the use of atovaquone or a salt thereof, and, optionally, proguanil or a salt thereof, for the treatment of various human diseases and conditions, including gastrointestinal disorders and, in particular, those associated with inflammation, such as inflammatory bowel disease (IBD), ulcerative colitis (UC), and Crohn's disease (CD).

9 Claims, No Drawings

USE OF ATOVAQUONE AND PROGUANIL FOR TREATMENT OF GASTROINTESTINAL DISEASES AND INFLAMMATION

CROSS-REFERENCE TO RELATED APPLICATIONS

This application is a continuation application of International Patent Application No. PCT/US2021/036207, filed on Jun. 7, 2021, which claims the benefit of priority to U.S. Provisional Application No. 63/036,308, filed on Jun. 8, 2020, the entire contents of each of which are expressly incorporated herein by reference.

BACKGROUND OF THE INVENTION

Research has shown that inflammation, a well-known process that protects the host from bacteria, viruses, toxins and infections, can also contribute to the pathogenesis of various human diseases. Although these diseases can be diverse in clinical manifestation and pathogenesis, they share the common factor of dysregulation of the normal immune response. Inflammatory bowel disease (IBD), including ulcerative colitis (UC) and Crohn's disease (CD), is a chronic inflammatory state affecting the gastrointestinal tract. The pathogenesis of IBD, including UC and CD, is complex and associated with various pathogenic factors such as a dysregulated pro-inflammatory immune response, abnormal gut microbiota, environmental changes, and gene variants. Although a full understanding of IBD pathogenesis remains unclear, conventional therapies attempt to alleviate clinical symptoms, control inflammation, prevent complications, and improve overall quality of life. Frequently, however, these conventional therapies fail, resulting in severe morbidity, incomplete resolution of symptoms, and often times the need for surgical intervention.

Curative treatments for diseases associated with chronic inflammation, such as IBD, are currently not available and treatments that are available are often poorly tolerated and have significant side effects. There remains a need for new therapies that are effective, safe, and well tolerated by patients.

SUMMARY OF THE INVENTION

The present disclosure provides methods of treating various human diseases and conditions using atovaquone or a salt thereof, proguanil or a salt thereof, or a combination thereof. As described herein, it has been discovered that atovaquone or a salt thereof, optionally, in combination with proguanil or a salt thereof can act as a potent therapy for treating diseases and conditions of the gastrointestinal tract, as well as those having an inflammatory component. In particular, it has been discovered that atovaquone or a salt thereof, proguanil or a salt thereof, or a combination thereof are useful for preventing and treating human diseases and conditions having a complex pathogenesis associated with multiple disparate factors, including, for example, a dysregulated pro-inflammatory immune response, abnormal gut microbiota, environmental changes, and gene variants. Further, it has been discovered that atovaquone or a salt thereof, proguanil or a salt thereof, or a combination thereof can act as a potent therapy for treating a gastrointestinal (GI) disease or condition. As described herein, treatment with atovaquone or a salt thereof, proguanil or a salt thereof, or a combination thereof can reduce the severity, frequency, and/or duration of a symptom associated with these diseases and conditions. In some instances, treatment with atovaquone or a salt thereof, proguanil or a salt thereof, or a combination thereof can also induce remission of the diseases and conditions, as described herein. Further, that atovaquone or a salt thereof, proguanil or a salt thereof, or a combination thereof can serve as effective therapy for subjects who have failed on, or who are unsuitable for treatment with, a conventional therapy, such as an immunosuppressant.

Accordingly, the present invention provides methods of treating various human diseases and conditions, as described herein, by administering to the subject an effective amount of atovaquone or a salt thereof, proguanil or a salt thereof, or a combination thereof.

In one aspect, the present invention provides methods of treating an inflammatory disease or condition in a subject in need thereof, comprising administering to the subject an effective amount of atovaquone, or a salt thereof.

In one aspect, the present invention provides methods of treating a gastrointestinal (GI) disease or condition in a subject in need thereof, comprising administering to the subject an effective amount of atovaquone, or a salt thereof.

In some embodiments, the methods further comprising administering to the subject an effective amount of proguanil, or a salt thereof.

In some embodiments, the inflammatory disease or condition is a gastrointestinal (GI) disease or condition. Alternatively, in some embodiments, the GI disease or condition is a non-inflammatory GI disease or condition.

In some embodiments, the GI disease or condition can be selected from the group consisting of an inflammatory bowel disease (IBD), an ulcerative colitis (UC), a Crohn's disease (CD), an irritable bowel syndrome (IBS), an indeterminate colitis (IC), a microscopic colitis, a collagenous colitis, a lymphocytic colitis, an incomplete microscopic colitis, and a segmental colitis associated with diverticula (SCAD).

In some embodiments, the GI disease or condition is an inflammatory bowel disease (IBD).

In some embodiments, the GI disease or condition is an ulcerative colitis (UC). For example, the UC can be selected from the group consisting of proctitis, left-sided colitis, total colitis, pancolitis, and extensive colitis.

In some embodiments, the GI disease or condition is a Crohn's disease (CD). For example, the CD can be selected from the group consisting of ileocecal, ileitis, jejunoileitis, Crohn's colitis, gastroduodenal, perianal, and oral Crohn's disease.

In some embodiments, the GI disease or condition is an irritable bowel syndrome (IBS). For example, the IBS can be selected from the group consisting of an IBS with constipation (IBS-C), an IBS with diarrhea (IBS-D), an IBS with mixed constipation and diarrhea (IBS-M), an IBS with alternating stool pattern (IBS-A), a post-infection (PI) IBS, and a post-diverticulitis IBS.

In some embodiments, the methods result in the attenuation of at least one symptom of a disease or condition as described herein.

In some embodiments, the methods reduce the severity, frequency, and/or duration of at least one symptom associated with an inflammatory disease or condition, optionally, wherein the methods induce remission of an inflammatory disease or condition.

In certain embodiments, the methods reduce the severity, frequency, and/or duration of at least one symptom associated with a GI disease or condition, optionally, wherein the methods induce remission of a GI disease or condition.

In certain embodiments, the methods result in the attenuation of at least one clinical feature associated with a GI disease or condition, optionally, selected from the group consisting of inflammation, jaundice, rectal bleeding, urgency, diarrhea, tenesmus, incontinence, fistula formation, constipation, bloating, abdominal cramps, colicky abdominal pain, change in bowel habit, mouth ulcers, anemia with associated symptoms of palpitations, dizziness, and dyspnea, fistulae, nausea, vomiting, fatigue, malaise, fever, and loss of weight or appetite.

In certain embodiments, the methods result in the attenuation of at least one lab abnormality, e.g., consistent with the presence of inflammation. For example, the at least one lab abnormality associated with the presence of inflammation can be selected from the group consisting of elevated erythrocyte sedimentation rate, elevated C-reactive protein, elevated white blood cell count, low iron, elevated stool inflammatory markers, malabsorption, metabolic bone disease, and radiographic evidence of inflammation.

In certain embodiments, the methods result in the attenuation of at least one endoscopic feature associated with a GI disease or condition, optionally, selected from the group consisting of erythema, petechiae, exudates, edema, loss of vascular pattern, cobblestone appearance, granularity, erosions, pseudopolyposis, ulcerations, stricture formation, pseudopolyposis, friability, contact bleeding, and spontaneous bleeding.

In some certain embodiments, the methods result in the attenuation of at least one pathological feature associated with a GI disease or condition, optionally, selected from the group consisting of distortion of crypt architecture, crypt abscesses, crypt branching, crypt atrophy, crypt disarray, crypt shortening, lamina propria and basal infiltration of leukocytes, mucin depletion, Paneth cell metaplasia, basal plasmacytosis, lymphoid aggregates, granulomas, ulcerations, and erosions.

In some embodiments, the methods further alleviate an extraintestinal manifestation and/or a complication associated with a GI disease or condition (e.g., IBD). An extraintestinal manifestation and/or complication associated with a GI disease or condition (e.g., IBD) can affect a subject's joints, bones, skin, eyes, cardiovascular system, pulmonary system, hepato-pancreatico-biliary system, and/or coagulopathy. Non-limiting examples of an extraintestinal manifestation and/or a complication associated with a GI disease or condition include a spondyloarthritis, an ankylosing spondylitis, central or axial arthritis, an erythema nodosum, a pyoderma gangrenosum, vulvar involvement, a psoriasis, an eczema, a episcleritis/scleritis, a uveitis, iritis, an infective endocarditis, a Takayasu's arteritis, a pericarditis, secondary amyloidosis, renal stones, bone loss, bronchiectasis, chronic bronchitis, interstitial lung disease, bronchiolitis obliterans with organizing pneumonia, cryptogenic organizing pneumonia, sarcoidosis, necrobiotic lung nodules, pulmonary infiltrates with eosinophilia syndrome, pulmonary embolus, a primary sclerosing cholangitis (PSC), primary biliary cholangitis (PBC), a nonalcoholic fatty liver disease (NAFLD), drug induced liver injury (e.g., from medications used to treat IBD), pyogenic liver abscess, granulomatous hepatitis, reactivation of viral hepatitis, portal vein thrombosis and a thromboembolism.

In some embodiments, the subject is suffering from a combination of GI diseases or conditions, optionally, wherein the subject is suffering from an inflammatory bowel disease (IBD), an ulcerative colitis (UC), an irritable bowel syndrome (IBS), and/or a segmental colitis associated with diverticula (SCAD).

In some embodiments, the disease or condition as described herein is refractory to treatment with a conventional therapy. For example, in some instances, an inflammatory disease or condition as described herein is refractory to a conventional therapy. In another example, a GI disease or condition as described herein is refractory to a conventional therapy.

In particular embodiments, the disease or condition is refractory to treatment with a conventional therapy comprises an anti-inflammatory agent, an immunosuppressant drug, an 5-aminosalicylate (5-ASA), a corticosteroid, a tumor necrosis factor (TNF)-alpha inhibitor, an alpha-4 integrin inhibitor, an IL-12 and IL-23 inhibitor, a biologic, a biosimilar, an antibiotic, a dietary supplement, a laxative, an antispasmodic, an antidepressant, anti-diarrheal medication, a pain medication, and/or a surgery.

In some embodiments, the conventional therapy comprises adalimumab (HUMIRA®), adalimumab-atto (AMJEVITA®), alosetron (LOTRONEX®), ampicillin (OMNIPEN®), azathioprine (AZASAN®, IMURAN®), balsalazide (COLAZAL®, GIAZOL®), cyclosporine (GENGRAF®, NEORAL®, SANDIMMUNER), certolizumab (CIMZIA®), ciprofloxacin (CIPRO®), eluxadoline (VIBERZI®), golimumab (SIMPONI®), infliximab (REMICADE®), infliximab-dyyb (INFLECTRA®), linaclotide (LINZESS®), lubiprostone (AMITIZAR), mesalamine (ASACOL®, CANASAR, DELZICOL®, LIALDAR, PENTASAR), 6-mercaptopurine (PURINETHOL®, PURIXAN®), methotrexate (TREXALL®, MTX®, RHEUMATREX®, MEXATER), methylprednisolone, metronidazole (FLAGYL®), natalizumab (TYSABRI®), olsalazine (DIPENTUM®), prednisone, rifaximin (XIFAXAN®), sulfasalazine (AZULFIDINE®), tacrolimus (PROGRAF®), tetracycline, ustekinumab (STELARA®), and/or vedolizumab (ENTYVIO®).

In some embodiments, the atovaquone, or salt thereof, is administered at a dosage of between about 0.5 mg to about 4,000 mg, about 100 mg to about 3,000 mg, about 500 mg to about 2000 mg or at about 1000 mg. For example, the atovaquone can be administered at a dosage of about 0.5 mg, about 1 mg, about 5 mg, about 10 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1,000 mg, about 1,250 mg, about 1,500 mg, about 1,750 mg, or about 2,000 mg, about 2,250 mg, about 2,500 mg, about 2,750 mg, about 3,000 mg, about 3,250 mg, about 3,500 mg, about 3,750 mg, about 4,000 mg of atovaquone, or a salt thereof. In certain embodiments, the dosage of atovaquone or a salt thereof is a daily dosage.

In some embodiments, the proguanil or a salt thereof is administered at a dosage of between about 0.5 mg to about 2,000 mg, about 50 mg to about 1500 mg, about 100 mg to about 1000 mg, or at about 400 mg. For example, the proguanil can be administered at a dosage of about 0.5 mg, about 1 mg, about 5 mg, about 10 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1,000 mg, about 1,250 mg, about 1,500 mg, about 1,750 mg, or about 2,000 mg of proguanil, or a salt thereof. In certain embodiments, the dosage of proguanil or a salt thereof is a daily dosage.

In some embodiments, the atovaquone or a salt thereof and/or the proguanil or a salt thereof is administered simultaneously, in the same or in separate compositions, or sequentially.

In some embodiments, the atovaquone or a salt thereof and/or the proguanil or a salt thereof is administered orally, optionally, as a liquid or a tablet.

In some embodiments, the atovaquone or a salt thereof and/or the proguanil or a salt thereof is administered at least every 6 hours, at least every 12 hours, at least once a day (e.g., as a single dose), or at least once every other day, optionally, wherein the composition is administered at least once a day (QD), at least twice a day (BID), at least three times a day (TID), or continuously.

In some embodiments, the atovaquone or a salt thereof and/or the proguanil or a salt thereof is administered for at least about 3 days to about 30 days, at least about 4 days to about 7 days, up to about 10 days, at least about 2 weeks, at least about 4 weeks, at least about 8 weeks, at least about 14 weeks, at least about 16 weeks, at least about 24 weeks, at least about 1 year, at least about 2 years, or the duration of the subject's life.

In preferred embodiments, the subject is human. In certain embodiments, the subject is not suitable for treatment with a conventional therapy, optionally, wherein the conventional therapy comprises an immunosuppressant, such as infliximab (REMICADE®) and/or vedolizumab (ENTYVIO®).

In certain embodiments, the subject has, or is at risk of having, a viral infection, such as a coronavirus infection (e.g., a SARS-COV-2 infection). In some embodiments, the subject has, or is at risk of having, coronavirus disease 2019 (COVID-19).

In some embodiments, the methods further comprise administering an additional therapy, such as a conventional therapy, to the subject. In some embodiments, the conventional therapy is for a GI disease or condition. In some embodiments, the additional therapy is administered simultaneously, in the same or in separate compositions, or sequentially.

The present invention is further illustrated by the following detailed description and drawings.

DETAILED DESCRIPTION OF THE INVENTION

The present invention is based, at least in part, on the discovery that administration of atovaquone or a salt thereof, proguanil or a salt thereof, or a combination thereof to a subject is effective in preventing and treating various diseases and conditions, e.g., a disease or condition related to, resulting from, or exacerbated by inflammation. In particular, it has been discovered that administration of atovaquone or a salt thereof, proguanil or a salt thereof, or a combination thereof to a subject is effective in reducing symptoms of a disease or condition of the gastrointestinal tract, such as an inflammatory bowel disease (IBD), ulcerative colitis (UC), Crohn's disease (CD), and/or irritable bowel syndrome (IBS). This discovery offers an attractive new treatment strategy for the large number of patients suffering from gastrointestinal inflammation, particularly chronic gastrointestinal inflammation, such as those patients suffering from IBD, UC, CD, and/or IBS, and particularly those patients for whom no satisfactory and effective treatment is currently available. Further, this discovery provides new and efficacious therapies in the field for treating diseases and conditions related to, resulting from, or exacerbated by increased inflammation in a subject. While atovaquone and proguanil have previously been used as effective treatments for other diseases, the finding that such agents can be used to treat inflammation, gastrointestinal diseases or conditions, and certain related diseases is surprising.

Accordingly, the present invention provides pharmaceutical compositions and methods of treating various human diseases and conditions, as described herein, by administering to the subject an effective amount of atovaquone or a salt thereof, proguanil or a salt thereof, or a combination thereof.

I. Definitions

Unless defined otherwise, all technical and scientific terms used herein have the same meaning as commonly understood by one of ordinary skill in the art to which the invention pertains.

In order that the present disclosure may be more readily understood, certain terms are first defined. In addition, it should be noted that whenever a value or range of values of a parameter are recited, it is intended that values and ranges intermediate to the recited values are also intended to be part of this disclosure.

The use of the terms "a" and "an" and "the" and similar referents in the context of describing the invention (especially in the context of the following claims) are to be construed to cover both the singular and the plural (i.e., one or more), unless otherwise indicated herein or clearly contradicted by context. In certain embodiments, the articles "a" and "an" are used herein to refer to one or to more than one (i.e., to at least one) of the grammatical object of the article. By way of example, "an element" means one element or more than one element, e.g., a plurality of elements. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value recited or falling within the range, unless otherwise indicated herein, and each separate value is incorporated into the specification as if it were individually recited.

The term "about" is used herein to mean within the typical ranges of tolerances in the art. For example, "about" can be understood as about 2 standard deviations from the mean. In certain embodiments, about means±20%. In certain embodiments, about means±10%. In certain embodiments, about means±5%. When about is present before a series of numbers or a range, it is understood that "about" can modify each of the numbers in the series or range.

The term "at least" prior to a number or series of numbers is understood to include the number adjacent to the term "at least", and all subsequent numbers or integers that could logically be included, as clear from context. When at least is present before a series of numbers or a range, it is understood that "at least" can modify each of the numbers in the series or range.

The term "including" is used herein to mean, and is used interchangeably with, the phrase "including but not limited to".

The term "or" is used herein to mean, and is used interchangeably with, the term "and/or," unless context clearly indicates otherwise.

As used herein, "no more than" or "less than" is understood as the value adjacent to the phrase and logical lower values or integers, as logical from context, to zero. When "no more than" is present before a series of numbers or a range, it is understood that "no more than" can modify each of the numbers in the series or range. As used herein, ranges include both the upper and lower limit.

As used herein, the term "substantially" refers to the qualitative condition of exhibiting total or near-total extent or degree of a characteristic or property of interest. One of ordinary skill in the art will understand that biological and chemical phenomena rarely, if ever, go to completion and/or proceed to completeness or achieve or avoid an absolute result. The term "substantially" may therefore be used in some embodiments herein to capture potential lack of completeness inherent in many biological and chemical phenomena.

The terms "therapeutically effective amount" or "effective amount," as used interchangeably herein, are intended to include the amount of an agent, e.g., atovaquone or a salt thereof, proguanil or a salt thereof, or a combination thereof that, when administered to a subject having a disease as described herein, is sufficient to effect a particular biological result, such as treatment of the disease (e.g., by diminishing, ameliorating, or maintaining the existing disease or one or more symptoms of disease). The "therapeutically effective amount" may vary depending on the agent, how the agent is administered, the disease and its severity and the history, age, weight, family history, genetic makeup, the types of preceding or concomitant treatments, if any, and other individual characteristics of the subject to be treated. Dosage regimens may be adjusted to provide the optimum therapeutic response. An "effective amount" is also one in which any toxic or detrimental effects (e.g., side effects) of a composition of atovaquone or a salt thereof, proguanil or a salt thereof, or a combination thereof are outweighed by the therapeutically beneficial effects. In some embodiments, an "effective amount" of atovaquone or a salt thereof, proguanil or a salt thereof, or a combination thereof refers to the level required to treat or prevent one or more symptoms of a disease or condition as described herein. In some embodiments, an "effective amount" is at least a minimal amount of atovaquone or a salt thereof, proguanil or a salt thereof, or a combination thereof, which is sufficient for treating or preventing one or more symptoms of a disease or condition as described herein. In some embodiments, an "effective amount" is that amount sufficient to substantially improve the likelihood of treating the inflammation or other symptom of a disease or condition as described herein, such as a gastrointestinal disease or condition.

"Prophylactically effective amount," as used herein, is intended to include the amount of an agent, e.g., atovaquone or a salt thereof, proguanil or a salt thereof, or a combination thereof that, when administered to a subject having a disease or condition as described herein, is sufficient to prevent or ameliorate the disease or one or more symptoms of the disease. Ameliorating the disease includes slowing the course of the disease or reducing the severity of later-developing disease. The "prophylactically effective amount" may vary depending on the agent, how the agent is administered, the degree of risk of disease, and the history, age, weight, family history, genetic makeup, the types of preceding or concomitant treatments, if any, and other individual characteristics of the patient to be treated.

A "therapeutically effective amount" or "prophylactically effective amount" also includes an amount of an agent, e.g., atovaquone or a salt thereof, proguanil or a salt thereof, or a combination thereof that produces some desired local or systemic effect at a reasonable benefit/risk ratio applicable to any treatment. An agent, e.g., atovaquone or a salt thereof, proguanil or a salt thereof, or a combination thereof, employed in the methods of the present disclosure may be administered in a sufficient amount to produce a reasonable benefit/risk ratio applicable to such treatment.

As used herein, the terms "treat", "treatment", and "treating" refer to the reduction or amelioration of the progression, severity and/or duration of any disease or condition, or the amelioration of one or more symptoms (preferably, one or more discernible symptoms) of any disease or condition resulting from the administration of one or more therapies (e.g., atovaquone or a salt thereof, proguanil or a salt thereof, or a combination thereof). In specific embodiments, the terms "treat", "treatment", and "treating" refer to the amelioration of at least one measurable physical parameter of any disease or condition, as described herein, which may or may not necessarily be discernible by the subject. In some embodiments, the terms "treat", "treatment", and "treating" refer to the inhibition of the progression of the disease or condition, either physically by, e.g., stabilization of a discernible symptom, physiologically by, e.g., stabilization of a physical parameter, or both. In some embodiments, the terms "treat", "treatment", and "treating" refer to the reduction or stabilization of the symptoms of the disease or condition. In some embodiments, the terms "treat", "treatment", and "treating" refer to preventing and/or delaying the onset of the disease or condition. In some embodiments, the terms "treat", "treatment", and "treating" refer to partially or completely alleviating, inhibiting, delaying onset of, reducing the incidence of, ameliorating and/or relieving a disease or condition as described herein, or one or more symptoms of a disease or condition as described herein. In some embodiments, the terms "treat", "treatment", and "treating" refer to inducing the remission of a disease or condition as described herein.

In some embodiments, the terms "treat", "treatment", and "treating" include prevention, that is, causing the clinical symptoms not to develop, preventing progression to a harmful state; (ii) inhibition, that is, arresting the development or further development of clinical symptoms, e.g., mitigating or completely inhibiting active (ongoing) inflammation so as to decrease inflammation, which decrease can include substantially complete elimination of inflammation; and/or (iii) relief, that is, causing the regression of clinical symptoms, e.g., causing relief from diarrhea, rectal bleeding and weight loss, reduction in colon lesions, reduction of strictures, reduction of fistulae, and/or reduction of colonic inflammation. In some embodiments, a clinical symptom may comprise a clinical feature, a lab abnormality, an endoscopic feature, and/or a pathological feature, e.g., as described herein.

Accordingly, in some embodiments, the term "treatment" or "treating" includes any administration of a composition described herein and includes: (i) preventing the disease from occurring in a subject which may be predisposed to the disease but does not yet experience or display the pathology or symptomatology of the disease; (ii) inhibiting the disease in an subject that is experiencing or displaying the pathology or symptomatology of the diseased (i.e., arresting further development of the pathology and/or symptomatology); or (iii) ameliorating the disease in a subject that is experiencing or displaying the pathology or symptomatology of the diseased (i.e., reversing the pathology and/or symptomatology).

In certain embodiments, "treatment," "prevention" or "amelioration" of a disease or condition includes delaying or preventing the onset of such a disease or condition, reversing, alleviating, ameliorating, inhibiting, slowing down or stopping the progression, aggravation or deterioration the progression, or severity of a condition associated with such a disease or condition. In one embodiment, the symptoms of a disease or condition are alleviated by at least 5%, at least 10%, at least 20%, at least 30%, at least 40%, or at least 50%.

Efficacy of treatment may be determined in association with any known method for diagnosing the disease or condition. Alleviation of one or more symptoms of the disease or condition indicates that the composition confers a clinical benefit. Any of the therapeutic methods described above can be applied to any suitable subject including, for example, mammals such as dogs, cats, cows, horses, rabbits, monkeys, and most preferably, humans.

"Treatment" can also mean prolonging survival as compared to expected survival in the absence of treatment.

As used herein, "prevention" or "preventing," when used in reference to a disease or condition, refers to a reduction in the likelihood that a subject will develop a symptom associated with such a disease or condition as described herein. The failure to develop a disease or condition, or the reduction in the development of a symptom associated with such a disease or condition (e.g., by at least about 10% on a clinically accepted scale for that disease or condition), or the exhibition of delayed symptoms delayed (e.g., by days, weeks, months or years) is considered effective prevention.

As used herein, "ameliorate," "amelioration," "improvement" or the like refers to, for example, a detectable improvement or a detectable change consistent with improvement that occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range between about any two of these values. Such improvement or change may be observed in treated subjects as compared to subjects not treated, e.g., with atovaquone or a salt thereof, proguanil or a salt thereof, or a combination thereof, where the untreated subjects have, or are subject to developing, the same or similar disease, condition, symptom or the like. Amelioration of a disease, condition, symptom or assay parameter may be determined subjectively or objectively, e.g., self-assessment by a subject (s), by a clinician's assessment or by conducting an appropriate assay or measurement. Amelioration may be transient, prolonged, or permanent, or it may be variable at relevant times during or after, e.g., atovaquone or a salt thereof, proguanil or a salt thereof, or a combination thereof is administered to a subject.

As used herein, a "subject" is an animal, such as a mammal, including a primate (such as a human, a non-human primate, e.g., a monkey, and a chimpanzee), or a non-primate (such as a rat, or a mouse). In a preferred embodiment, the subject is a human, such as a human being treated or assessed for a disease or condition that would benefit from administration of atovaquone or a salt thereof, proguanil or a salt thereof, or a combination thereof; a human at risk for a disease or condition that would benefit from administration of atovaquone or a salt thereof, proguanil or a salt thereof, or a combination thereof; a human having a disease or condition that would benefit from administration of atovaquone or a salt thereof, proguanil or a salt thereof, or a combination thereof; or human being treated for a disease or condition that would benefit from atovaquone or a salt thereof, proguanil or a salt thereof, or a combination thereof as described herein.

The terms "administration" or "administering" include routes of introducing a composition(s) of atovaquone or a salt thereof, proguanil or a salt thereof, or a combination thereof to a subject to perform their intended function. In embodiments where both atovaquone, or a salt thereof, and proguanil, or a salt thereof, are administered, they may be administered as distinct compositions, whether concurrently or separately, or administered as a formulation that includes both atovaquone, or a salt thereof, and proguanil, or a salt thereof. As used herein, administration of composition(s) of atovaquone, or a salt thereof, proguanil, or a salt thereof, or combinations thereof are intended to include administration by injection (subcutaneous, intravenous, parenterally, intraperitoneally, intrathecal), oral, subcutaneous, rectal, and/or transdermal routes. The pharmaceutical preparations may be given by forms suitable for each administration route. For example, these preparations are administered in tablet or capsule form, ointment, suppository, and administration by injection or infusion; topical by lotion or ointment; and rectal by suppositories. In some embodiments, oral administration is preferred. The injection can be bolus or can be continuous infusion. Depending on the route of administration, a composition(s) of atovaquone or a salt thereof, proguanil or a salt thereof, or a combination thereof can be coated with or disposed in a selected material to protect it from natural conditions that may detrimentally affect its ability to perform its intended function. A composition(s) of atovaquone or a salt thereof, proguanil or a salt thereof, or a combination thereof can be administered alone, or in conjunction with either another agent or therapy as described herein or with a pharmaceutically-acceptable carrier, or both. A composition(s) of atovaquone, or a salt thereof, proguanil, or a salt thereto, or a combination thereof can be administered prior to the administration of the other agent or therapy, simultaneously with the agent or therapy, or after the administration of the agent or therapy. In certain embodiments, the subject is administered the pharmaceutical composition as described herein at least once a day. In certain embodiments, the subject is administered the pharmaceutical composition as described herein at least twice a day. In certain embodiments, the subject is administered the pharmaceutical composition as described herein at least three times a day. In other embodiments, the subject is administered the pharmaceutical composition up to once a day. In other embodiments, the subject is administered the pharmaceutical composition up to twice a day. In other embodiments, the subject is administered the pharmaceutical composition up to three times a day. In certain embodiments, the subject is administered the pharmaceutical composition not more than once a day. In certain embodiments, the subject is administered the pharmaceutical composition not more than twice a day. In certain embodiments, the subject is administered the pharmaceutical composition not more than three times a day. In certain embodiments, the subject is administered the pharmaceutical composition as needed. In certain embodiments, the subject is administered the pharmaceutical composition as needed, but not more than once a day. In certain embodiments, the subject is administered the pharmaceutical composition as needed, but not more than twice a day. In certain embodiments, the subject is administered the pharmaceutical composition as needed, but not more than three times a day.

Administration "in combination with" one or more further therapeutic agents or therapies include simultaneous (concurrent) and consecutive administration in any order.

As will be readily apparent to one skilled in the art, the useful in vivo dosage to be administered and the particular mode of administration will vary depending upon the age, weight and mammalian species treated, the particular compounds employed, and the specific use for which these compounds are employed. Typically, human clinical applications of products are commenced at lower dosage levels, with dosage level being increased until the desired effect is achieved.

"Refractory" as used herein refers to a disease or condition, as described herein, that does not respond to a treatment. In embodiments, a refractory disease or condition can be resistant to a treatment before or at the beginning of the treatment. In some embodiments, the refractory disease or condition can become resistant during a treatment. A subject "responds" to treatment if a parameter of a disease or condition (e.g., a symptom, such as inflammation) in the subject is retarded or reduced by a detectable amount, e.g., about 5%, 10%, 20%, 30%, 40%, 50%, 60%, 70%, 80%, 90% or more as determined by any appropriate measure. In one example, a subject responds to treatment if the subject experiences a life expectancy extended by about 5%, 10%, 20%, 30%, 40%, 50% or more beyond the life expectancy predicted if no treatment is administered. In another example, a subject responds to treatment, if the subject has an increased disease-free survival, overall survival or increased time to progression. Several methods, as known in the art and described herein, can be used to determine if a patient responds to a treatment. These methods can also be used to determine whether remission has been achieved.

The term "pharmaceutically acceptable" is employed herein to refer to those compounds, materials, compositions, or dosage forms which are, within the scope of sound medical judgment, suitable for use in contact with the tissues of human subjects and animal subjects without excessive toxicity, irritation, allergic response, or other problem or complication, commensurate with a reasonable benefit/risk ratio.

The term "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the subject being treated. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates or polyanhydrides; (22) bulking agents, such as polypeptides and amino acids (23) serum component, such as serum albumin, HDL and LDL; and (22) other non-toxic compatible substances employed in pharmaceutical formulations.

The term "sample," as used herein, includes a collection of similar fluids, cells, or tissues isolated from a subject, as well as fluids, cells, or tissues present within a subject. Examples of biological fluids include blood, serum and serosal fluids, plasma, cerebrospinal fluid, ocular fluids, lymph, urine, feces, saliva, and the like. Tissue samples may include samples from tissues, organs or localized regions. For example, samples may be derived from particular organs, parts of organs, or fluids or cells within those organs. In certain embodiments, samples may be derived from the gastrointestinal tract. In some embodiments, the sample is a biopsy sample.

The term "inflammatory bowel disease" or "IBD," as used herein, describes a group of chronic relapsing and remitting inflammatory diseases of the gastrointestinal tract, of which the two primary subgroups are Crohn's disease (CD) and ulcerative colitis (UC). The primary distinction between CD and UC are the location and nature of the inflammatory lesions. CD lesions can appear anywhere in the gastrointestinal tract, from mouth to anus, whereas in UC they typically appear in the colon and rectum. While CD in adults typically manifests in the terminal ileum, in children the appearance is not so limited. While the inflammatory lesions of CD are discontinuous, transmural (affecting all layers of the bowel wall), and often granulomatous, in UC they are limited to the mucosal (epithelial lining of the gut). Patients with IBD are also much more likely to have other chronic inflammatory diseases, including primary sclerosing cholangitis, ankylosing spondylitis, psoriasis and multiple sclerosis, amongst others. Urlep et al, Minerva Gastroenterol. Dietol. 51:147-63 (2005). In some embodiments, IBD symptoms may include, without limitation, inflammation of the intestine and resulting in abdominal cramping and persistent diarrhea. Inflammatory bowel diseases include, but are not limited to, ulcerative colitis (UC), Crohn's disease (CD), indeterminate colitis (IC), chronic colitis, discontinuous or patchy disease, ileal inflammation, extracolonic inflammation, granulomatous inflammation in response to ruptured crypts, aphthous ulcers, transmural inflammation, microscopic colitis, diverticulitis and diversion colitis.

The term "ulcerative colitis" or "UC", as used herein, refers to a condition involving inflammation of the large intestine and rectum. In patients with UC, there is an inflammatory reaction primarily involving the colonic mucosa. The inflammation is typically uniform and continuous with no intervening areas of normal mucosa. Surface mucosal cells as well as crypt epithelium and submucosa are involved in an inflammatory reaction with neutrophil infiltration. Ultimately, this reaction typically progresses to epithelial damage and loss of epithelial cells resulting in multiple ulcerations, fibrosis, dysplasia and longitudinal retraction of the colon.

The term "Crohn's disease" or "CD", as used herein, to refers to a condition involving chronic inflammation of the gastrointestinal tract. Crohn's-related inflammation usually affects the intestines, but may occur anywhere from the mouth to the anus. CD differs from UC in that the inflammation extends through all layers of the intestinal wall and involves mesentery as well as lymph nodes. The disease is often discontinuous, i.e., severely diseased segments of bowel are separated from apparently disease-free areas. In CD, the bowel wall also thickens which can lead to obstructions and the development of fistulas and fissures are not uncommon. As used herein, CD may be one or more of several types of CD, including without limitation, ileocolitis (affects the ileum and the large intestine); ileitis (affects the ileum); gastroduodenal CD (inflammation in the stomach and the duodenum); jejunoileitis (spotty patches of inflammation in the jejunum); and Crohn's (granulomatous) colitis (only affects the large intestine).

The term "irritable bowel syndrome" or "IBS", as used herein, includes a group of functional bowel diseases or conditions characterized by one or more symptoms including, but not limited to, abdominal pain, abdominal discomfort, change in bowel pattern, loose or more frequent bowel movements, diarrhea, and constipation, typically in the absence of any apparent structural abnormality. There are at least three forms of IBS, depending on which symptom predominates: (1) diarrhea-predominant (IBS-D); (2) constipation-predominant (IBS-C); and (3) IBS with alternating stool pattern (IBS-A). IBS can also occur in the form of a mixture of symptoms (IBS-M). There are also various clinical subtypes of IBS, such as post-infectious IBS (IBS-PI) and a post-diverticulitis IBS. In some embodiments, IBS can be associated with inflammation. In certain embodiments, IBS is associated with inflammation in subjects with diarrhea-predominant (IBS-D) or with presumed post-infectious IBS (IBS-PI). When IBS is associated with inflammation, mucosal immune system activation may be characterized by alterations in particular immune cells and markers. For example, in some embodiments, an increased numbers of lymphocytes may be present in the colon and/or small intestine of a subject with IBS. In other embodiments, an increased number of mast cells may be present in the terminal ileum, jejunum, and/or colon of a subject with IBS. In some embodiments, elevated levels of plasma pro-inflammatory interleukins may be present in subjects with IBS. In other embodiments, IBS is not associated with inflammation.

II. Therapeutic Agents

In an embodiment, the pharmaceutical compositions and methods of treatment described herein include one or more active agents. Atovaquone, or a salt thereof, may be an active agent provided at an amount and/or dosage described herein in the pharmaceutical compositions and methods of treatment of the invention. Proguanil, or a salt thereof, may be an active agent provided in an amount and/or dosage described herein in the pharmaceutical compositions and methods of treatment of the invention. In some embodiments, a combination of atovaquone, or a salt thereof, and proguanil, or a salt thereof, may be provided at an amount and/or dosage described herein in the pharmaceutical compositions and methods of treatment of the invention.

In some embodiments, the dosages described herein can comprise a single dosage or a daily dosage.

In some embodiments, a combination comprising atovaquone, or a salt thereof, and proguanil, or a salt thereof, can be administered simultaneously, in the same or in separate compositions, or sequentially. In certain preferred embodiments, atovaquone, or a salt thereof, and/or proguanil, or a salt thereof, can be administered orally, optionally, as a liquid or a tablet.

In particular embodiments, the atovaquone, or a salt thereof, and/or proguanil, or a salt thereof, is administered at least every 6 hours, at least every 12 hours, at least once a day (e.g., as a single dose), or at least once every other day, optionally, wherein the composition is administered at least once a day (QD), at least twice a day (BID), at least three times a day (TID), or continuously. In some embodiments, atovaquone, or a salt thereof, and/or proguanil, or a salt thereof, can be administered for at least about 3 days to about 30 days, at least about 4 days to about 7 days, up to about 10 days, at least about 2 weeks, at least about 4 weeks, at least about 8 weeks, at least about 14 weeks, at least about 16 weeks, at least about 24 weeks, at least about 1 year, at least about 2 years, or the duration of the subject's life.

Atovaquone

Atovaquone is an anti-pneumocystic and antiprotozoal drug disclosed in U.S. Pat. No. 5,053,432 and European Patent No. 0123238, which are incorporated herein by reference. The chemical name of atovaquone is trans-2-[4-(4-chlorophenyl) cyclohexyl]-3-hydroxy-1,4-naphthalenedione. Atovaquone is a yellow crystalline solid that is practically insoluble in water. It has a molecular weight of 366.84 g/mol and the molecular formula $C_{22}H_{19}ClO_3$. The compound has the following structural formula:

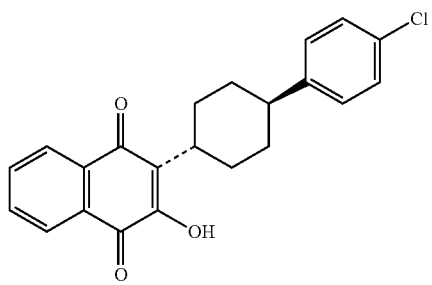

Atovaquone is available in the market, e.g., under the trade names MEPRON®, MALARONE®, and MALARONE PEDIATRIC®. MEPRON® is available in the form of an oral suspension (e.g., at a dosage of 750 mg/5 mL) or a tablet (e.g., at a dosage of 250 mg per tablet). MEPRON® is indicated for the prevention and treatment of *Pneumocystis carinii* pneumonia (PCP), toxoplasmosis, and babesiosis. MALARONE® and MALARONE PEDIATRIC® are the combination products of atovaquone with proguanil hydrochloride which are available in the form of a tablet (e.g., at a dosage of 250 mg atovaquone and 100 mg proguanil hydrochloride for MALARONE®, and at a dosage of 62.5 mg atovaquone and 25 mg proguanil hydrochloride for MALARONE PEDIATRIC®). MALARONE® and MALARONE PEDIATRIC® are indicated for the prophylaxis and treatment of *Plasmodium falciparum* malaria.

European Patent No. 0362996, which is incorporated herein by reference, discloses the use of atovaquone in the treatment and/or prophylaxis of *Pneumocystis carinii* pneumoni, using formulations suitable for pulmonary administration containing naphthoquinone particles having a diameter in the range 0.5 to 7 μm. European Patent Nos. 0445141 and 0496729, which are incorporated herein by reference, disclose the uses of atovaquone against toxoplasmosis and cryptosporidiosis, respectively. U.S. Pat. No. 6,018,080, which is incorporated herein by reference, discloses microfluidized particles of atovaquone, a method for their preparation and a pharmaceutical composition containing the same and its use in therapy. U.S. Pat. Nos. 6,018,080 and 6,649,659, which are incorporated herein by reference, disclose atovaquone particles having particle sizes in the range of 0.1-3 μm and the method of their preparation using a microfluidizer. U.S. Pat. Nos. 5,998,449 and 6,166,046, which are incorporated herein by reference, disclose combinations of atovaquone and proguanil for use in the treatment and prophylaxis of parasitic infections. U.S. Pat. Nos. 7,847,127 and 8,598,387, which are incorporated herein by reference, discloses processes for the preparation of atovaquone and intermediates thereof. U.S. Pat. No. 9,169,232, which is incorporated herein by reference, discloses an atovaquone prodrug compound.

In some embodiments, the pharmaceutical compositions and methods described herein may include atovaquone, or a salt thereof, in a therapeutically effective amount. In some embodiments, the pharmaceutical compositions and methods described herein may include a derivative of atovaquone, or a salt thereof, in a therapeutically effective amount. In some embodiments, the atovaquone may be MEPRON®, MALARONE®, or MALARONE PEDIATRIC®.

In some embodiments, the pharmaceutical compositions and methods described herein may include atovaquone, or a salt thereof, at a dosage of between about 0.5 mg to about 4,000 mg, about 100 mg to about 3,000 mg, about 500 mg to about 2000 mg or at about 1000 mg. In some embodiments, the atovaquone, or salt thereof, is administered at a dosage of about 0.5 mg, about 1 mg, about 5 mg, about 10 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1,000 mg, about 1,250 mg, about 1,500 mg, about 1,750 mg, or about 2,000 mg, about 2,250 mg, about 2,500 mg, about 2,750 mg, about 3,000 mg, about 3,250 mg, about 3,500 mg, about 3,750 mg, about 4,000 mg of atovaquone, or a salt thereof.

In some embodiments, the pharmaceutical composition and methods described herein may include atovaquone or a salt thereof in an amount of at least about 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, or 4000 mg.

In some embodiments, the pharmaceutical composition and methods described herein may include atovaquone or a salt thereof in an amount of at most about 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, or 4000 mg.

In some embodiments, the pharmaceutical composition and methods described herein may include atovaquone or a salt thereof in an amount of about 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, or 4000 mg.

In some embodiments, the pharmaceutical composition and methods described herein may include atovaquone or a salt thereof in an amount to provide a dosage to the subject of about 0.01 mg/kg to about 80 mg/kg, about 1 mg/kg to about 100 mg/kg, about 5 mg/kg to about 75 mg/kg, about 25 mg/kg to about 75 mg/kg, or about 30 mg/kg to about 40 mg/kg.

In some embodiments, the pharmaceutical composition and methods described herein may include atovaquone or a salt thereof in an amount to provide a dosage to the subject of at least about 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, or 4000 mg/kg.

In some embodiments, the pharmaceutical composition and methods described herein may include atovaquone or a salt thereof in an amount of at most about 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, or 4000 mg/kg.

In some embodiments, the pharmaceutical composition and methods described herein may include atovaquone or a salt thereof in an amount of about 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, or 4000 mg/kg.

In some embodiments, atovaquone for use in pharmaceutical compositions and methods described herein may be provided in any of a variety of forms. For example, forms of atovaquone suitable for use herein include pharmaceutically acceptable salts, prodrugs, polymorphs (i.e., crystal forms), co-crystals, hydrates, solvates, and the like.

Proguanil

Proguanil, also known as chlorguanide and chloroguanide, is an antimalarial. The synthesis of which is disclosed in US20110263901, which is incorporated herein by reference. The chemical name of proguanil is N-(4-chlorophenyl)-N'-(1-methylethyl) imidodicarbonimidic diamide. Proguanil has a molecular weight of 253.73 g/mol and the molecular formula of $C_{11}H_{16}ClN_5$. The compound has the following structural formula:

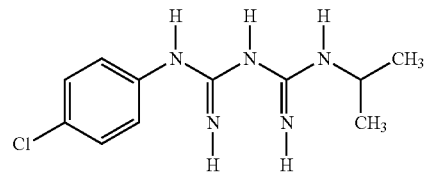 [SMILES: CC(C)NC(=N)NC(=N)Nc1ccc(Cl)cc1]

Proguanil also has the chemical name 1-(4-chlorophenyl)-5-isopropyl-biguanide. It is commercially available as a hydrochloride salt. Proguanil hydrochloride is a white crystalline solid that is sparingly soluble in water. It has a molecular weight of 290.22 and the molecular formula C11H16ClN5·HCl.

Proguanil is available in the market, e.g., under the trade name Paludrine®. Paludrine® is available in the form of a tablet (e.g., at a dosage of 100 mg of proguanil hydrochloride). Paludrine® is indicated for the prophylaxis of malaria. Proguanil is a prodrug that primarily exerts its effect by means of its active metabolite cycloguanil, which functions as a dihydrofolate reductase inhibitor. Inhibition of dihydrofolate reductase in the malaria parasite disrupts deoxythymidylate synthesis. Malarone® and Malarone Pediatric® are the combination products of atovaquone with proguanil hydrochloride.

In some embodiments, the pharmaceutical compositions and methods described herein may include proguanil, or a salt thereof, in a therapeutically effective amount. In some embodiments, the pharmaceutical compositions and methods described herein may include an active metabolite of proguanil, e.g., cycloguanil, in a therapeutically effective amount. In some embodiments, the pharmaceutical compositions and methods described herein may include a derivative of proguanil, or a salt thereof, in a therapeutically effective amount. In some embodiments, the proguanil, or a salt thereof, may be PALUDRINE®, MALARONE®, or MALARONE PEDIATRIC®.

In some embodiments, the pharmaceutical compositions and methods described herein may include proguanil, or a salt thereof, at a dosage of between about 0.5 mg to about 2,000 mg, about 50 mg to about 1500 mg, about 100 mg to about 1000 mg, or at about 400 mg. In some embodiments, the proguanil, or salt thereof, is administered at a dosage of about 0.5 mg, about 1 mg, about 5 mg, about 10 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1,000 mg, about 1,250 mg, about 1,500 mg, about 1,750 mg, or about 2,000 mg of proguanil, or a salt thereof.

In some embodiments, the pharmaceutical composition and methods described herein may include proguanil, or a salt thereof, in an amount of at least about 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, 1000, 1100, 1200, 1300, 1400, 1500, 1600, 1700, 1800, 1900, 2000 mg.

In some embodiments, the pharmaceutical composition and methods described herein may include proguanil, or a salt thereof, in an amount of at most about 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, 1000, 1100, 1200, 1300, 1400, 1500, 1600, 1700, 1800, 1900, 2000 mg.

In some embodiments, the pharmaceutical composition and methods described herein may include proguanil, or a salt thereof, in an amount of about 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, 1000, 1100, 1200, 1300, 1400, 1500, 1600, 1700, 1800, 1900, 2000 mg.

In some embodiments, the pharmaceutical composition and methods described herein may include proguanil, or a salt thereof, in an amount to provide a dosage to the subject of about 0.01 mg/kg to about 80 mg/kg, about 1 mg/kg to about 100 mg/kg, about 5 mg/kg to about 75 mg/kg, about 25 mg/kg to about 75 mg/kg, or about 30 mg/kg to about 40 mg/kg.

In some embodiments, the pharmaceutical composition and methods described herein may include proguanil, or a salt thereof, in an amount to provide a dosage to the subject of at least about 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, 1000, 1100, 1200, 1300, 1400, 1500, 1600, 1700, 1800, 1900, 2000 mg/kg.

In some embodiments, the pharmaceutical composition and methods described herein may include proguanil, or a salt thereof, in an amount to provide a dosage to the subject of at most about 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, 1000, 1100, 1200, 1300, 1400, 1500, 1600, 1700, 1800, 1900, 2000 mg/kg.

In some embodiments, the pharmaceutical composition and methods described herein may include proguanil, or a salt thereof, in an amount to provide a dosage to the subject of about 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, 1000, 1100, 1200, 1300, 1400, 1500, 1600, 1700, 1800, 1900, 2000 mg/kg.

In some embodiments, proguanil for use in pharmaceutical compositions and methods described herein may be provided in any of a variety of forms. For example, forms of proguanil suitable for use herein include pharmaceutically acceptable salts, prodrugs, polymorphs (i.e., crystal forms), co-crystals, hydrates, solvates, active metabolites, and the like.

III. Pharmaceutical Compositions

In some embodiments, the invention includes pharmaceutical compositions including an active agent for treating a disease or condition, e.g., as described herein. In some embodiments, the pharmaceutical composition for treating disease may include a therapeutically effective amount of atovaquone or a salt thereof, a therapeutically effective amount of proguanil or a salt thereof, or a combination thereof and a pharmaceutically acceptable carrier. In some embodiments, the pharmaceutical composition for treating disease may include atovaquone or a salt thereof in an amount or dosage described herein, proguanil or a salt thereof in an amount or dosage described herein, and a pharmaceutically acceptable carrier. In some embodiments, the pharmaceutically acceptable carrier may include one or more of the carriers or excipients described herein.

Pharmaceutical compositions described herein may be suitable for administration by injection (e.g., subcutaneous, intravenous, parenterally, intraperitoneally, and/or intrathecal), oral, subcutaneous, rectal, and/or transdermal routes. The pharmaceutical preparations may be given by forms suitable for each administration route.

In particular embodiments, the pharmaceutical compositions described herein may be suitable for oral administration and can be presented as discrete dosage forms, such as capsules, sachets, tablets, liquids, or aerosol sprays each containing a predetermined amount of an active ingredient as a powder or in granules, a solution, or a suspension in an aqueous or non-aqueous liquid, an oil-in-water emulsion, a water-in-oil liquid emulsion, powders for reconstitution, powders for oral consumptions, bottles (including powders or liquids in a bottle), orally dissolving films, lozenges, pastes, tubes, gums, and packs. Such dosage forms can be prepared by any of the methods of pharmacy, but all methods include the step of bringing the active ingredient(s) into association with the carrier, which constitutes one or more necessary ingredients. In general, the pharmaceutical compositions are prepared by uniformly and intimately admixing the active ingredient(s) with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The invention further encompasses anhydrous pharmaceutical compositions and dosage forms since water can facilitate the degradation of some compounds. For example, water may be added in the pharmaceutical arts as a means of simulating long-term storage in order to determine characteristics such as shelf-life or the stability of pharmaceutical compositions over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, pharmaceutical compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

The active agents can be combined in an intimate admixture with a pharmaceutical carrier according to conventional pharmaceutical compounding techniques. The carrier can take a wide variety of forms depending on the form of preparation desired for administration. In preparing the pharmaceutical compositions for an oral dosage form, any of the usual pharmaceutical media can be employed as carriers, such as, for example, water, glycols (e.g., propylene glycol), oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pregelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the pharmaceutical compositions of the invention to provide tablets that disintegrate when exposed to an aqueous environment. Too much of a disintegrant may produce tablets which disintegrate in the bottle. Too little may be insufficient for disintegration to occur, thus altering the rate and extent of release of the active ingredients from the dosage form. Thus, a sufficient amount of disintegrant that is neither too little nor too much to detrimentally alter the release of the active ingredient(s) may be used to form the dosage forms of the active agents disclosed herein. The amount of disintegrant used may vary based upon the type of pharmaceutical composition and mode of administration, and may be readily discernible to those of ordinary skill in the art. About 0.5 to about 15 weight percent of disintegrant, or about 1 to about 5 weight percent of disintegrant, may be used in the pharmaceutical compositions. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, sodium stearyl fumarate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl aureate, agar, or mixtures thereof. Additional lubricants include, for example, a syloid silica gel, a coagulated aerosol of synthetic silica, silicified microcrystalline cellulose, or mixtures thereof. A lubricant can optionally be added in an amount of less than about 0.5% or less than about 1% (by weight) of the pharmaceutical composition.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Pharmaceutical compositions for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactants which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

In an embodiment, the pharmaceutical compositions may include a solubilizer to ensure good solubilization and/or dissolution of the compound of the present invention and to minimize precipitation of the compound of the present invention. A solubilizer may also be added to increase the solubility of the hydrophilic drug and/or other components, such as surfactants, or to maintain the pharmaceutical composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinyl alcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, E-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, caprolactone and isomers thereof, 8-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but are not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropylmethyl cellulose, hydroxypropyl cyclodextrins, ethanol, polyethylene glycol 200-100, glycofurol, transcutol, propylene glycol, and dimethyl isosorbide.

The pharmaceutical compositions described herein can further include one or more pharmaceutically acceptable additives. Such additives include, without limitation, detackifiers, antifoaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

IV. Methods of the Invention

In certain aspects, the present invention provides methods for treating a disease or condition in a subject in need thereof that includes administering a therapeutically effective amount of atovaquone or a salt thereof, a therapeutically effective amount of proguanil or a salt thereof, or a combination thereof. In some embodiments, the present invention includes a method for treating a disease or condition in a subject in need thereof that includes administering a pharmaceutical composition, as described herein, comprising a therapeutically effective amount of atovaquone or a salt thereof and/or a therapeutically effective amount of proguanil or a salt thereof with a pharmaceutically acceptable carrier. In some embodiments, the methods described herein can further comprise administering an additional therapy to the subject in need thereof. In some embodiments, the additional therapy can be a conventional therapy known in the art. In some embodiments, the additional therapy can be administered simultaneously, in the same or in separate compositions, or sequentially.

Treating Chronic Inflammation and Inflammatory Diseases

In some embodiments, the disease or condition to be treated may be one associated with inflammation. In some embodiments, the disease may be a condition that results from, is exacerbated by, or is otherwise related to inflammation. In some embodiments, the disease may be a condition that may be treated or alleviated by correcting (e.g., reducing) inflammation. In some embodiments, the disease or condition that may be treated or alleviated by correcting inflammation may be an inflammatory disease or condition, e.g., as described herein. In some embodiments, the disease or condition that may be treated or alleviated by correcting inflammation may be a gastrointestinal (GI) disease or condition, e.g., as described herein. In some embodiments, the invention may include a method of treating increased inflammation in a subject in need thereof, by administering a therapeutically effective amount of a therapeutic agent selected from the group consisting of atovaquone or a salt thereof, proguanil or a salt thereof, and a combination thereof. In some embodiments, the invention may include a method of reducing inflammation in a subject in need thereof, by administering a therapeutically effective amount of a therapeutic agent selected from the group consisting of atovaquone or a salt thereof, proguanil or a salt thereof, and a combination thereof.

In some embodiments, the invention may include methods of treating an inflammatory disease or condition in a subject in need thereof, comprising administering to the subject an effective amount of atovaquone or a salt thereof. In some embodiments, the inflammatory disease or condition is a gastrointestinal (GI) disease or condition. Optionally, the method further includes administering to the subject an effective amount of proguanil or a salt thereof.

In some embodiments, treating a subject suffering from an inflammation, e.g., a chronic inflammation, includes reducing or eliminating in a subject a clinical symptom of a chronic inflammation and/or delaying or preventing in a subject the onset of a clinical symptom of a chronic inflammation. For example, treating can include reducing a symptom of a condition characterized by a chronic inflammation by, e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%.

The symptoms associated with chronic inflammation are well known and can be determined by a person of ordinary skill in the art by taking into account factors, including, but not limited to, the location of the chronic inflammation, the cause of the chronic inflammation, the severity of the chronic inflammation, and/or the tissue or organ affected by the chronic inflammation. Those of skill in the art will know the appropriate symptoms or indicators associated with a specific type of chronic inflammation and will know how to determine if an individual is a candidate for treatment as disclosed herein. In some embodiments, chronic inflammation symptoms include, but are not limited to, edema, hyperemia, erythema, bruising, tenderness, stiffness, swollenness, fever, fibrosis, chills, stuffy nose, stuffy head, breathing problems, fluid retention, blood clots, loss of appetite, increased heart rate, formation of granulomas, fibrinous, pus, non-viscous serous fluid, ulcers, and pain.

An inflammation symptom, such as a chronic inflammation symptom, can be associated with and contribute to the pathogenesis of a large, unrelated group of human diseases and conditions, including, for example, many immune system diseases or conditions resulting in abnormal inflammation as well as non-immune diseases with etiological origins in chronic inflammatory processes.

In some embodiments, the methods reduce the severity, frequency, and/or duration of at least one symptom associated with an inflammatory disease or condition, optionally, wherein the methods induce remission of an inflammatory disease or condition, as described herein.

Non-limiting examples of diseases and conditions (e.g., inflammatory diseases and conditions) associated with chronic inflammation that may be treated according to a method described herein include acne, acid reflux/heartburn, age related macular degeneration (AMD), allergy, allergic rhinitis, Alzheimer's disease, amyotrophic lateral sclerosis, anemia, appendicitis, arteritis, arthritis, asthma, atherosclerosis, autoimmune diseases or conditions, balanitis, blepharitis, bronchiolitis, bronchitis, a bullous pemphigoid, burn, bursitis, cancer, cardiac arrest, carditis, celiac disease, cellulitis, cervicitis, cholangitis, cholecystitis, chorioamnionitis, chronic obstructive pulmonary disease (COPD), cirrhosis, colitis, congestive heart failure, conjunctivitis, Crohn's disease, cyclophosphamide-induced cystitis, cystic fibrosis, cystitis, common cold, dacryoadenitis, dementia, dermatitis, dermatomyositis, diabetes, diabetic neuropathy, diabetic retinopathy, diabetic nephropathy, diabetic ulcer, digestive system disease, eczema, emphysema, encephalitis, endocarditis, endometritis, enteritis, enterocolitis, epicondylitis, epididymitis, fasciitis, fibromyalgia, fibrosis, fibrositis, gastritis, gastroenteritis, gingivitis, glomerulonephritis, glossitis, heart disease, heart valve dysfunction, hepatitis, hidradenitis suppurative, Huntington's disease, hyperlipidemic pancreatitis, hypertension, ileitis, infection, inflammatory bowel disease, inflammatory cardiomegaly, inflammatory neuropathy, insulin resistance, interstitial cystitis, interstitial nephritis, iritis, ischemia, ischemic heart disease, keratitis, keratoconjunctivitis, laryngitis, lupus nephritis, mastitis, mastoiditis, meningitis, metabolic syndrome (syndrome X), a migraine, multiple sclerosis, myelitis, myocarditis, myositis, nephritis, neurodegenerative diseases, non-alcoholic steatohepatitis, obesity, omphalitis, oophoritis, orchitis, osteochondritis, osteopenia, osteomyelitis, osteoporosis, osteitis, otitis, pancreatitis, Parkinson's disease, parotitis, pelvic inflammatory disease, pemphigus vulgaris, pericarditis, peritonitis, pharyngitis, phlebitis, pleuritis, pneumonitis, polycystic nephritis, proctitis, progressive supranuclear palsy, prostatitis, psoriasis, pulpitis, pyelonephritis, pylephlebitis, renal failure, reperfusion injury, retinitis, rheumatic fever, rhinitis, salpingitis, sarcoidosis, sialadenitis, sinusitis, spastic colon, stenosis, stomatitis, stroke, surgical complication, synovitis, tendonitis, tendinosis, tenosynovitis, thrombophlebitis, tonsillitis, trauma, traumatic brain injury, transplant rejection, trigonitis, tuberculosis, tumor, ulcerative colitis, urethritis, uveitis, vaginitis, vasculitis, and vulvitis.

In one embodiment, a chronic inflammation comprises a tissue inflammation that is confined to a particular tissue or organ. In some embodiments, a tissue inflammation comprises, e.g., a skin inflammation, a muscle inflammation, a tendon inflammation, a ligament inflammation, a bone inflammation, a cartilage inflammation, a lung inflammation, a heart inflammation, a liver inflammation, a pancreatic inflammation, a kidney inflammation, a bladder inflammation, a stomach inflammation, an intestinal inflammation, a neuron inflammation, and a brain inflammation.

In another embodiment, a chronic inflammation comprises a systemic inflammation, such as inflammation due to infection (i.e., sepsis), including bacteremia (i.e., bacterial sepsis) and viremia (i.e., viral sepsis).

In another embodiment, a chronic inflammation comprises an arthritis. Arthritis includes a group of conditions involving damage to the joints of the body due to the inflammation of the synovium including, without limitation osteoarthritis, rheumatoid arthritis, juvenile idiopathic arthritis, spondyloarthropathies like ankylosing spondylitis, reactive arthritis (Reiter's syndrome), psoriatic arthritis, enteropathic arthritis associated with inflammatory bowel disease, Whipple disease and Behcet disease, septic arthritis, gout (also known as gouty arthritis, crystal synovitis, metabolic arthritis), pseudogout (calcium pyrophosphate deposition disease), and Still's disease. Arthritis can affect a single joint (monoarthritis), two to four joints (oligoarthritis) or five or more joints (polyarthritis) and can be either an auto-immune disease or a non-autoimmune disease.

In another embodiment, a chronic inflammation comprises an autoimmune disease or condition. Autoimmune diseases can be broadly divided into systemic and organ-specific (local) autoimmune diseases or conditions, depending on the principal clinico-pathologic features of each disease. Systemic autoimmune diseases include, without limitation, systemic lupus erythematosus (SLE), Sjogren's syndrome, Scleroderma, rheumatoid arthritis and polymyositis. Local autoimmune diseases may be endocrinologic (Diabetes Mellitus Type 1, Hashimoto's thyroiditis, Addison's disease etc.), dermatologic (pemphigus vulgaris), hematologic (autoimmune hemolytic anemia), neural (multiple sclerosis) or can involve virtually any circumscribed mass of body tissue. Non-limiting examples of autoimmune diseases or conditions include acute disseminated encephalomyelitis (ADEM), Addison's disease, an allergy or sensitivity, amyotrophic lateral sclerosis, anti-phospholipid antibody syndrome (APS), arthritis, autoimmune hemolytic anemia, autoimmune hepatitis, autoimmune inner ear disease, autoimmune pancreatitis, bullous pemphigoid, celiac disease, Chagas disease, chronic obstructive pulmonary disease (COPD), diabetes mellitus type 1 (IDDM), endometriosis, fibromyalgia, Good pastures syndrome, Graves' disease, Guillain-Barre syndrome (GBS), Hashimoto's thyroiditis, hidradenitis suppurativa, idiopathic thrombocytopenia purpura, inflammatory bowel disease, interstitial cystitis, lupus (including discoid lupus erythematosus, drug-induced lupus erythematosus. lupus nephritis, neonatal lupus, subacute cutaneous lupus erythematosus and systemic lupus erythematosus), morphea, multiple sclerosis (MS), myasthenia gravis, myopathies, narcolepsy, neuromyotonia, pemphigus vulgaris, pernicious anemia, primary biliary cirrhosis, recurrent disseminated encephalomyelitis (multiphasic disseminated encephalomyelitis), rheumatic fever, schizophrenia, scleroderma, Sjogren's syndrome, tenosynovitis, vasculitis, and vitiligo.

In another embodiment, a chronic inflammation comprises a myopathy. Myopathies are caused when the immune system inappropriately attacks components of the muscle, leading to inflammation in the muscle. A myopathy includes an inflammatory myopathy and an auto-immune myopathy. Myopathies include, without limitation, dermatomyositis, inclusion body myositis, and polymyositis.

In another embodiment, a chronic inflammation comprises a vasculitis. Vasculitis is a varied group of diseases and conditions featuring inflammation of a vessel wall including lymphatic vessels and blood vessels like veins (phlebitis), arteries (arteritis) and capillaries due to leukocyte migration and resultant damage. The inflammation may affect any size blood vessel, anywhere in the body. It may affect either arteries and/or veins. The inflammation may be focal, meaning that it affects a single location within a vessel; or it may be widespread, with areas of inflammation scattered throughout a particular organ or tissue, or even affecting more than one organ system in the body. Vasculitis include, without limitation, Buerger's disease (thromboangiitis obliterans), cerebral vasculitis (central nervous system vasculitis), Churg-Strauss arteritis, cryoglobulinemia, essential cryoglobulinemic vasculitis, giant cell (temporal) arteritis, Golfer's vasculitis, Henoch-Schonlein purpura, hypersensitivity vasculitis (allergic vasculitis), Kawasaki disease, microscopic polyarteritis/polyangiitis, polyarteritis nodosa, polymyalgia rheumatica (PMR), rheumatoid vasculitis, Takayasu arteritis, Wegener's granulomatosis, and vasculitis secondary to connective tissue disorders like systemic lupus erythematosus (SLE), rheumatoid arthritis (RA), relapsing polychondritis, Behcet's disease, or other connective tissue disorders, vasculitis secondary to viral infection.

In another embodiment, a chronic inflammation comprises a skin disease or condition. Skin diseases and conditions include, without limitation, an acne, including acne vulgaris, a bullous pemphigoid, a dermatitis, including atopic dermatitis and chronic actinic dermatitis, an eczema like atopic eczema, contact eczema, xerotic eczema, seborrheic dermatitis, dyshidrosis, discoid eczema, venous eczema, dermatitis herpetiformis, neurodermatitis, autoeczematization, stasis dermatitis, hidradenitis suppurativa, lichen planus, psoriasis including plaque psoriasis, nail psoriasis, guttate psoriasis, scalp psoriasis, inverse psoriasis, pustular psoriasis, erythrodermic psoriasis, and psoriatic arthritis, rosacea and scleroderma including morphea.

In another embodiment, a chronic inflammation comprises a gastrointestinal (GI) disease or condition. A GI disease or condition is a disease or condition related to the gastrointestinal tract, e.g., the esophagus, stomach, small intestine, large intestine, rectum, and the accessory organs of digestion, including the liver, gallbladder, and pancreas. GI diseases and conditions include, without limitation, such conditions as constipation, diarrhea, gas-bloat syndrome, nausea, vomiting, esophagitis, gastritis, enteritis, gastroesophageal reflux disease (GERD), irritable bowel syndrome, hemorrhoids, anal fissures, perianal abscesses, anal fistulas, perianal infections, diverticular diseases, colitis, colon polyps, and cancer. Further, a GI disease or condition includes, without limitation, irritable bowel syndrome (IBS), an inflammatory bowel disease (IBD) including Crohn's disease (CD) and an ulcerative colitis (UC).

In another embodiment, a chronic inflammation comprises a cardiovascular disease. Non-limiting examples of cardiovascular diseases or conditions include a hypertension, endocarditis, myocarditis, heart valve dysfunction, congestive heart failure, myocardial infarction, diabetic cardiac conditions, blood vessel inflammation like arteritis, phlebitis, vasculitis; arterial occlusive disease like arteriosclerosis and stenosis, inflammatory cardiomegaly, a peripheral arterial disease; an aneurysm; an embolism; a dissection; a pseudoaneurysm; a vascular malformation; a vascular nevus; a thrombosis; a thrombophlebitis; varicose veins; a stroke. Symptoms of a cardiovascular disease or condition affecting the heart include, without limitation, chest pain or chest discomfort (angina), pain in one or both arms, the left shoulder, neck, jaw, or back, shortness of breath, dizziness, faster heartbeats, nausea, abnormal heartbeats, feeling fatigued. Symptoms of a cardiovascular disease or condition affecting the brain include, without limitation, sudden numbness or weakness of the face, arm, or leg, especially on one side of the body, sudden confusion or trouble speaking or understanding speech, sudden trouble seeing in one or both eyes, sudden dizziness, difficulty walking, or loss of balance or coordination, sudden severe headache with no known cause. Symptoms of a cardiovascular disease or condition affecting the legs, pelvis and/or arm include, without limitation, claudication, which is a pain, ache, or cramp in the muscles, and cold or numb feeling in the feet or toes, especially at night.

In another embodiment, a chronic inflammation comprises a cancer. Exemplary cancers in include a bladder tumor, breast tumor, prostate tumor, basal cell carcinoma, biliary tract cancer, bladder cancer, bone cancer, brain and CNS cancer (e.g., glioma tumor), cervical cancer, choriocarcinoma, colon and rectum cancer, connective tissue cancer, cancer of the digestive system, endometrial cancer, esophageal cancer, eye cancer, cancer of the head and neck, gastric cancer, intra-epithelial neoplasm, kidney cancer, larynx cancer, leukemia, liver cancer, lung cancer (e.g., small cell and non-small cell), lymphoma including Hodgkin's and Non-Hodgkin's lymphoma, melanoma, myeloma, neuroblastoma, oral cavity cancer (e.g., lip, tongue, mouth, and pharynx), ovarian cancer, pancreatic cancer, retinoblastoma, rhabdomyosarcoma, rectal cancer, renal cancer, cancer of the respiratory system, sarcoma, skin cancer, stomach cancer, testicular cancer, thyroid cancer, uterine cancer, cancer of the urinary system, as well as other carcinomas and sarcomas.

In another embodiment, a chronic inflammation comprises a drug-induced inflammation.

In another embodiment, a chronic inflammation comprises an infection, such as bacterial cystitis, bacterial encephalitis, pandemic influenza, viral encephalitis, and viral hepatitis (A, B and C).

In another embodiment, a chronic inflammation comprises a tissue or organ injury, such as a burn, a laceration, a wound, a puncture, or a trauma.

In another embodiment, a chronic inflammation comprises a transplant rejection.

In another embodiment, a chronic inflammation comprises a chronic neurogenic inflammation.

In some embodiments, the inflammatory disease or condition is refractory to a conventional therapy.

Treating Gastrointestinal (GI) Diseases and Conditions

The invention provides methods for treating and preventing gastrointestinal (GI) diseases and conditions in a subject in need thereof by administering a therapeutically effective amount of atovaquone or a salt thereof, proguanil or a salt thereof, or a combination thereof. The gastrointestinal disease or condition can be any in the art, and can include gastrointestinal diseases and conditions of the upper and/or lower gastrointestinal tracts, e.g., the esophagus, stomach, small intestine, large intestine, rectum, and the accessory organs of digestion, including the liver, gallbladder, and pancreas.

Gastrointestinal diseases and conditions include, but are not limited to, such conditions as constipation, diarrhea (e.g., Brainerd diarrhea), gas-bloat syndrome, enteritis, esophagitis, hemorrhoids, anal fissures, perianal abscesses, anal fistulas, perianal infections, diverticular diseases, colitis, colon polyps, ulcers, dyspepsia, acute gastrointestinal bleeding, lower esophageal mucosal rings, esophageal strictures, esophageal dismotility, hiatal hernia, achalasia, irritable bowel syndrome (IBS), Barrett's esophagus, gastroparesis, gastrointestinal motility disorders, celiac disease, IgA deficiency related GI disease, diverticulosis, diverticulitis, malabsorption syndromes, gastroesophageal reflux disease (GERD), problems caused by gastric bypass surgery, belching, eructation, flatulence, diarrhea, inflammatory bowel disease (IBD), ulcerative colitis (UC), Crohn's disease (CD), an indeterminate colitis (IC), a microscopic colitis, a collagenous colitis, a lymphocytic colitis, an incomplete microscopic colitis, and a segmental colitis associated with diverticula (SCAD), infectious enteritis, idiopathic gastric acid hypersecretion, gastritis, constipation, colic, vomiting, nausea, cyclic vomiting syndrome, cannabinoid hyperemesis syndrome, motion sickness, gastrointestinal injuries, esophageal injuries, gastric mucosal injuries, short bowel syndrome, bowel dysfunctions, early satiety, abdominal pain, abdominal bloating, sour stomach, radiation-induced injury to the gastrointestinal tract, gastrointestinal diseases or conditions induced by medications, chronic sore throat, noncardiac chest pains, coughing, dysphagia, Shwachman syndrome, decreased gastric mucin production, iron deficiency anemia, cystic fibrosis, cancer, pancreatitis, cholangitis, cholecystitis, cirrhosis, and the like.

In certain embodiments, the GI disease or condition can be selected from the group consisting of an inflammatory bowel disease (IBD), an ulcerative colitis (UC), a Crohn's disease (CD), an irritable bowel syndrome (IBS), an indeterminate colitis (IC), a microscopic colitis, a collagenous colitis, a lymphocytic colitis, an incomplete microscopic colitis, and a segmental colitis associated with diverticula (SCAD).

In some embodiments, the GI disease or condition is a non-inflammatory GI disease or condition.

In some embodiments, the GI disease or condition is associated with inflammation, e.g., chronic inflammation.

In particular embodiments, the GI disease or condition is an inflammatory bowel disease (IBD).

In particular embodiments, the GI disease or condition is an ulcerative colitis (UC). For example, the UC can be selected from the group consisting of proctitis, left-sided colitis, total colitis, pancolitis, and extensive colitis.

In particular embodiments, the GI disease or condition is a Crohn's disease (CD). For example, the CD can be selected from the group consisting of ileocecal, ileitis, jejunoileitis, Crohn's colitis, gastroduodenal, perianal, and oral Crohn's disease.

In some embodiments, the GI disease or condition is an irritable bowel syndrome (IBS). For example, the IBS can be selected from an IBS with constipation (IBS-C), an IBS with diarrhea (IBS-D), an IBS with mixed constipation and diarrhea (IBS-M), a post-infection (PI) IBS, and a post-diverticulitis IBS.

In some embodiments, the GI disease or condition is refractory to a conventional therapy, as described herein.

In some embodiments, the invention may include methods of treating a gastrointestinal (GI) disease or condition in a subject in need thereof, comprising administering to the subject an effective amount of atovaquone, or a salt thereof. Optionally, the method further includes administering to the subject an effective amount of proguanil, or a salt thereof.

In some embodiments, the invention may include methods of treating a gastrointestinal (GI) disease or condition in a subject in need thereof, comprising administering to the subject an effective amount of proguanil, or a salt thereof. Optionally, the method further includes administering to the subject an effective amount of atovaquone, or a salt thereof.

In some embodiments, the invention may include a method of treating an inflammatory bowel disease (IBD) or a symptom thereof in a subject in need thereof, by administering a therapeutically effective amount of a therapeutic agent selected from the group consisting of atovaquone, or a salt thereof, proguanil, or a salt thereof, and a combination thereof.

In some embodiments, the invention may include a method of treating an ulcerative colitis (UC) or a symptom thereof in a subject in need thereof, by administering a therapeutically effective amount of a therapeutic agent selected from the group consisting of atovaquone, or a salt thereof, proguanil, or a salt thereof, and a combination thereof.

In some embodiments, the invention may include a method of treating a Crohn's disease (CD) or a symptom thereof in a subject in need thereof, by administering a therapeutically effective amount of a therapeutic agent selected from the group consisting of atovaquone, or a salt thereof, proguanil, or a salt thereof, and a combination thereof.

In some embodiments, the invention may include a method of treating an irritable bowel syndrome (IBS) or a symptom thereof in a subject in need thereof, by administering a therapeutically effective amount of a therapeutic agent selected from the group consisting of atovaquone, or a salt thereof, proguanil, or a salt thereof, and a combination thereof.

In certain embodiments, the methods result in the attenuation of at least one clinical feature associated with a GI disease or condition. Exemplary clinical features associated with a GI disease or condition include, but are not limited to, inflammation, jaundice, rectal bleeding, urgency, diarrhea, tenesmus, incontinence, fistula formation, constipation, bloating, abdominal cramps, colicky abdominal pain, change in bowel habit, mouth ulcers, anemia with associated symptoms of palpitations, dizziness, and dyspnea, fistulae, nausea, vomiting, fatigue, malaise, fever, and loss of weight or appetite.

In certain embodiments, the methods result in the attenuation of at least one lab abnormality associated with the presence of inflammation. Exemplary lab abnormalities associated with the presence of inflammation include, but are not limited to, elevated erythrocyte sedimentation rate, elevated C-reactive protein, elevated white blood cell count, low iron, elevated stool inflammatory markers (e.g., calprotectin, lactoferrin, and/or eosinophil-derived neurotoxin), malabsorption, metabolic bone disease, and radiographic evidence of inflammation. In some embodiments, elevated erythrocyte sedimentation rate, elevated C-reactive protein, and elevated white blood cell count, and/or low iron are present in patients with IBD. In some embodiments, elevated stool inflammatory markers (e.g., calprotectin, lactoferrin, and/or eosinophil-derived neurotoxin), e.g., in the absence of detected pathogens, are present in patients with IBD. In some embodiments, radiographic evidence of UC or CD can include bowel inflammation and thickening, structuring, and internal fistula formation as well as detection of abscesses and enlarged lymph nodes. In some embodiments, malabsorption may be present as indicated by the presence of protein calorie malnutrition, hypocalcemia, vitamin deficiency (e.g., B12, D), and/or metabolic bone disease, especially in patients with Crohn's disease.

In some embodiments, the methods result in the attenuation of at least one endoscopic feature associated with a GI disease or condition. Exemplary endoscopic features associated with a GI disease or condition include, but are not limited to erythema, petechiae, exudates, edema, loss of vascular pattern, cobblestone appearance, granularity, erosions, pseudopolyposis, ulcerations, stricture formation, pseudopolyposis, friability, contact bleeding, and spontaneous bleeding. For example, in UC, distribution of endoscopic changes can be rectal, rectal and left sided to the splenic flexure (left sided ulcerative colitis), beyond the splenic flexure and the cecum (pancolitis). Occasionally, in some embodiments, a subset of patients with UC can have an area of focal inflammation around the appendiceal orifice that is not contiguous with disease elsewhere in the colon (so-called "cecal patch"). In Crohn's disease, in some embodiments, the inflammation in the GI tract can be most commonly in the ileum and colon in a patchy distribution but may affect anywhere in the entire luminal GI tract from the mouth to the anus.

In some embodiments, the methods result in the attenuation of at least one pathological feature associated with a GI disease or condition. Exemplary pathological features associated with a GI disease or condition include, but are not limited to distortion of crypt architecture, crypt abscesses, crypt branching, crypt atrophy, crypt disarray, crypt shortening, lamina propria and basal infiltration of leukocytes, mucin depletion, Paneth cell metaplasia, basal plasmacytosis, lymphoid aggregates, granulomas, ulcerations, and erosions.

In some embodiments, the methods described herein reduce the severity, frequency, and/or duration of at least one symptom associated with a GI disease or condition, optionally, wherein the methods induce remission of a GI disease or condition. Several methods, as known in the art, can be used to determine if a subject having a GI disease or condition responds to a treatment, e.g., as described herein. These methods can also be used to determine whether a method described herein induces remission of the GI disease or condition.

For example, in some embodiments, the Crohn's Disease Activity Index can be used to determine if a patient responds to a treatment, as described herein. The terms "Crohn's Disease Activity Index" and "CDAI" includes a research tool used to quantify the symptoms of patients with Crohn's disease (CD) (see, e.g., Best W R, et al. Gastroenterology. 70 (3): 439-444, 1976). The CDAI is generally used to define response or remission of CD. The CDAI consists of eight factors, each summed after adjustment with a weighting factor. The components of the CDAI and weighting factors are the following: (i) number of liquid or soft stools each day for seven days ×2; (ii) abdominal pain (graded from 0-3 on severity) each day ×5 for seven days; (iii) general wellbeing, subjectively assessed from 0 (well)×7 to 4 (terrible) each day for seven days; (iv) presence of complications*×20; (v) taking Lomitil or opiates for diarrhea ×30; (vi) presence of an abdominal mass (0 as none, 2 as ×10 questionable, 5 as definite); (vii) hematocrit of <0.47 in men and <0.42 in women ×6; and (viii) percentage deviation from standard weight ×1. * One point each is added for each set of complications: (i) the presence of joint pains (arthralgia) or frank arthritis; (ii) inflammation of the iris or uveitis; (iii) presence of erythema nodosum, pyoderma gangrenosum, or aphthous ulcers; (iv) anal fissures, fistulae or abscesses; (v) other fistulae; and/or (vi) fever during the previous week. Remission of Crohn's disease is typically defined as a fall in the CDAI to less than 150 points. Severe disease is typically defined as a value of greater than 450 points. In certain aspects, response to a particular medication in a Crohn's disease patient is defined as a fall of the CDAI of greater than 70 points.

For example, in some embodiments, the Harvey-Bradshaw index can be used to determine if a patient responds to a treatment, as described herein. The term "Harvey-Bradshaw index" includes a simpler version of the CDAI for data collection purposes (see, e.g., Harvey R, et al. Lancet. 1 (8167): 514, 1980). In some embodiments, it consists of only clinical parameters: (i) general well-being (0=very well, 1=slightly below average, 2=poor, 3=very poor, 4=terrible); (ii) abdominal pain (0=none, 1=mild, 2=moderate, 3=severe); (iii) number of liquid stools per day; (iv) abdominal mass (0=none, 1=dubious, 2=definite, 3=tender); and (v) complications, as above, with one point for each. In some embodiments, a score of less than 5 is generally considered to represent clinical remission. In some embodiments, a Simple Index of Crohn's disease activity can also be used (see, e.g., Elliott P N, et al. Lancet. 1 (8173): 876, 1980).

For example, in some embodiments, the Inflammatory Bowel Disease Questionnaire (IBDQ) can be used to determine if a patient responds to a treatment, as described herein. The terms "Inflammatory Bowel Disease Questionnaire" and "IBDQ" refers to a questionnaire for health-related quality of life (HRQOL) assessment in patients with inflammatory bowel diseases (IBDs), including ulcerative colitis (UC) and Crohn's disease (CD). In some embodiments, it consists of 32 questions divided into four dimensions: bowel symptoms (10 items), systemic symptoms (5 items), emotional function (12 items) and social function (5 items). Every question has graded responses from 1 (worst situation) to 7 (best situation), and thus the total score is ranging from 32 to 224 with higher scores representing better quality of life (see, e.g., Guyatt G, et al. Gastroenterology. 96 (3): 804-10, 1989).

For example, in some embodiments, the Mayo Score/Disease Activity Index (DAI) for Ulcerative Colitis can be used to determine if a patient responds to a treatment, as described herein. In some embodiments, the terms "Mayo Score/Disease Activity Index (DAI) for Ulcerative Colitis", "Mayo Score for Ulcerative Colitis" and "DAI for Ulcerative Colitis" includes a research tool used to endoscopically grade ulcerative colitis (UC) activity (see, e.g., Peyrin-Biroulet L, et al. Clin Gastroenterol Hepatol. 14 (3): 348-354.e17, 2016; Schroeder K W, et al. N Engl J Med. 317 (26): 1625-9, 1987). In some embodiments, it consists of an evaluation of clinical parameters including: (i) stool frequency (0-3); (ii) rectal bleeding (0-3); (iii) endoscopic findings (0-3); and physician global assessment (0-3). In some embodiments, a grade of "0" is normal, "1" is mild, "2" is moderate UC, and "3" is severe UC.

For example, in some embodiments, the Rome IV Criteria can be used to determine if a patient responds to a treatment, as described herein. In some embodiments, the terms "Rome IV Criteria" or "Rome Criteria" includes a research tool used to evaluate a patient with irritable bowel syndrome (see, e.g., Fass R, et al. *Archives of Internal Medicine.* 161 (17): 2081-8, 2001; Talley NJ. *Reviews in Gastroenterological Disorders.* 6 (2): 72-82, 2006). The Rome IV criteria includes recurrent abdominal pain, on average, at least 1 day/week in the last 3 months, associated with two or more of the following criteria: (i) related to defecation, (ii) associated with a change in frequency of stool, and (iii) associated with a change in form (appearance) of stool.

In some embodiments, the methods further alleviate an extraintestinal manifestation and/or a complication associated with a GI disease or condition (e.g., IBD). An extraintestinal manifestation and/or a complication associated with a GI disease or condition (e.g., IBD) can affect a subject's joints, bones, skin, eyes, cardiovascular system, pulmonary system, hepato-pancreatico-biliary system, and/or coagulopathy. Exemplary extraintestinal manifestation and/or a complication associated with a GI disease or condition include, but are not limited to, a spondyloarthritis, an ankylosing spondylitis, central or axial arthritis, an erythema nodosum, a pyoderma gangrenosum, vulvar involvement, a psoriasis, an eczema, a episcleritis/scleritis, a uveitis, iritis, an infective endocarditis, a Takayasu's arteritis, a pericarditis, secondary amyloidosis, renal stones, bone loss, bronchiectasis, chronic bronchitis, interstitial lung disease, bronchiolitis obliterans with organizing pneumonia, cryptogenic organizing pneumonia, sarcoidosis, necrobiotic lung nodules, pulmonary infiltrates with eosinophilia syndrome, pulmonary embolus, a primary sclerosing cholangitis (PSC), primary biliary cholangitis (PBC), a nonalcoholic fatty liver disease (NAFLD), drug induced liver injury (e.g., from medications used to treat IBD), pyogenic liver abscess, granulomatous hepatitis, reactivation of viral hepatitis, portal vein thrombosis and a thromboembolism.

Subjects

Exemplary subjects that may treat with a pharmaceutical composition or method of the present invention include, but are not limited to, those suffering from a disease or condition as described herein. In particular embodiments, the subject is human. In some embodiments, the subject is suffering from an inflammation, such as a chronic inflammation, as described herein. In some embodiments, the subject is suffering from an inflammatory disease or condition, as described herein. In some embodiments, the subject is suffering from a gastrointestinal (GI) disease or condition, as described herein. The subject can suffering from any combination of diseases and conditions, e.g., as describe herein, such as a combination of GI diseases and/or conditions, optionally, wherein the subject is suffering from an inflammatory bowel disease (IBD), an ulcerative colitis (UC), an irritable bowel syndrome (IBS), a segmental colitis associated with diverticula (SCAD), and/or colonic polyps.

In some embodiments, the subject is not suitable for treatment with a conventional therapy, as described herein. In some embodiments, the subject has failed to respond to treatment with a conventional therapy, as described herein. In some embodiments, the conventional therapy comprises an anti-inflammatory agent, an immunosuppressant drug, a 5-aminosalicylate (5-ASA), a corticosteroid, a tumor necrosis factor (TNF)-alpha inhibitor, an alpha-4 integrin inhibitor, an IL-12 and IL-23 inhibitor, a biologic, a biosimilar, an antibiotic, a dietary supplement, a laxative, an antispasmodic, an antidepressant, anti-diarrheal medication, a pain medication, and/or a surgery. In some embodiments, the conventional therapy comprises adalimumab (HUMIRA®), adalimumab-atto (AMJEVITA®), alosetron (LOTRONEX®), ampicillin (OMNIPEN®), azathioprine (AZASAN®, IMURAN®), balsalazide (COLAZAL®, GIAZOL®), cyclosporine (GENGRAF®, NEORAL®, SANDIMMUNE®), certolizumab (CIMZIA®), ciprofloxacin (CIPRO®), eluxadoline (VIBERZI®), golimumab (SIMPONI®), infliximab (REMICADE®), infliximab-dyyb (INFLECTRA®), linaclotide (LINZESS®), lubiprostone (AMITIZA®), mesalamine (ASACOL®, CANASA®, DELZICOL®, LIALDA®, PENTASA®), 6-mercaptopurine (PURINETHOL®, PURIXAN®), methotrexate (TREXALL®, MTX®, RHEUMATREX®, MEXATE®), methylprednisolone, metronidazole (FLAGYL®), natalizumab (TYSABRI®), olsalazine (DIPENTUM®), prednisone, rifaximin (XIFAXAN®), sulfasalazine (AZULFIDINE®), tacrolimus (PROGRAF®), tetracycline, ustekinumab (STELARA®), and/or vedolizumab (ENTYVIO®).

In certain embodiments, the subject is not suitable for treatment with a conventional therapy comprising an immunosuppressant, such as infliximab (REMICADE®) and/or vedolizumab (ENTYVIO®). Without wishing to be bound by any particular theory, a subject that has, or is at risk of having, a viral infection may not be suitable for treatment with some conventional therapies. For example, in the context of a viral infection, administration of an immunosuppressant may result in a subject that has, or is at risk of having, a viral infection to suffer a more severe course of the viral infection and its symptoms. Accordingly, the pharmaceutical compositions and methods of administering a therapeutically effective amount of atovaquone or a salt thereof, proguanil or a salt thereof, or a combination thereof can function as effective alternatives therapies for treating such patients.

Accordingly, in some embodiments, the invention provides methods of treating a subject who is not suitable for and/or who has failed to respond to a conventional therapy, as described herein. In particular embodiments, the subject is has, or is at risk of having, a viral infection. In some embodiments, the subject has, or is at risk of having, a coronavirus infection, such as a SARS-COV-2 infection. In certain embodiments, the subject has, or is at risk of having, coronavirus disease 2019 (COVID-19).

V. Kits

Any of the compositions described herein may be comprised in a kit. In a non-limiting example, the kit comprises an effective amount of atovaquone or a salt thereof, and/or proguanil or a salt thereof.

The kit may further include reagents or instructions for using the atovaquone or a salt thereof, and/or the proguanil or a salt thereof in a subject. It may also include one or more buffers or pharmaceutically acceptable carriers. In some embodiments, kit may further comprise an additional therapy as described herein.

The components of the kits may be packaged in any suitable form. The container means of the kits will generally include at least one vial, test tube, flask, bottle, syringe, or other container means, into which a component may be placed, and preferably, suitably aliquoted. Where there is more than one component in the kit (labeling reagent and label may be packaged together), the kit also will generally contain a second, third or other additional container into which the additional components may be separately placed. The kits may also comprise a second container means for containing a sterile, pharmaceutically acceptable buffer and/or other diluent. However, various combinations of components may be comprised in a container, such as a vial. The kits of the present invention also will typically include a means for containing the compositions of the invention, e.g., the atovaquone or a salt thereof, and/or the proguanil or a salt thereof, and any other reagent containers in close confinement for commercial sale.

When the components of the kit are provided in one and/or more liquid solutions, the liquid solution is an aqueous solution, with a sterile aqueous solution being particularly preferred. However, the components of the kit may be provided in the form of one or more tablets or capsule. In some embodiments, the components of the kit may be dried powder(s). When reagents and/or components are provided as a dry powder, the powder can be reconstituted by the addition of a suitable solvent. It is envisioned that the solvent may also be provided in another container means.

Unless otherwise defined, all technical and scientific terms used herein have the same meaning as commonly understood by one of ordinary skill in the art to which this invention belongs. Although methods and materials similar or equivalent to those described herein can be used in the practice or testing of the therapeutic agents and methods featured in the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1. Use of Atovaquone and Proguanil for the Treatment of Ulcerative Colitis Ulcerative Colitis (UC) is a chronic, inflammatory condition of the colon that is often difficult to treat. Atovaquone is an antiprotozoal agent and when combined with the antimalarial proguanil, it is used for the prevention and treatment of malaria and other parasitic diseases. Described herein, is a case of a middle aged man who used atovaquone-proguanil successfully to induce remission of a newly diagnosed ulcerative colitis that had been refractory to conventional therapy.

INTRODUCTION

The pathogenesis of Inflammatory Bowel Disease (IBD), comprising ulcerative colitis and Crohn's disease, is complex and incompletely understood. A dysregulated proinflammatory immune response underlies both diseases causing uncontrolled intestinal inflammation. Frequently, conventional medical therapy fails, causing severe morbidity and sometimes, the need for surgical intervention. New therapies that are effective, safe, and well tolerated are needed. The case of a 47 year old man with newly diagnosed severe ulcerative colitis that was refractory to conventional therapy is presented.

Case

A 47 year old male gastroenterologist presented with moderate to severe colitis symptoms. His past GI history included symptoms that had always been attributed to irritable bowel syndrome. Namely, he would get self-limited left lower quadrant pain with urgency and non-bloody diarrhea with varying frequency, usually related to food triggers. Due to a family history of colon polyps, screening colonoscopy was done at age 41 and revealed left sided diverticulosis with superficial predominantly crescentic erythema within the inter-diverticular mucosa of the sigmoid colon with rectal sparing. Biopsies revealed a non-specific focal active inflammatory process and a diagnosis of segmental colitis associated with diverticulosis (SCAD) was made. Five years later, at age 46, he developed a severe, non-bloody diarrheal illness that lasted for 3 weeks. Stool calprotectin was >2000 but cultures for routine pathogens, assays for *Clostridioides difficile* toxin, and examination for ova and parasites were negative. The illness resolved spontaneously. One month later, he underwent repeat screening colonoscopy which found worsening and more extensive erythema of the left colon and proximal rectum endoscopically with again, a non-specific focal active colitis on biopsy. SCAD remained the diagnosis.

Fourteen months later, he presented with crampy, postprandial left lower quadrant abdominal pain accompanied by urgency and loose stools. This progressed over several days to bloody diarrhea with tenesmus, mucous, worsening pain, bloating and fatigue. Thinking he likely had an infectious colitis, he empirically self-treated with a 10 day course of rifaximin 275 mg TID (he split 550 mg tablets). His symptoms persisted during and after the course of treatment. At this point, he consulted with his gastroenterologist who recommended a trial of mesalamine. He took APRISO® (mesalamine) 1.5 grams per day for 2 days while awaiting his generic mesalamine 1.2 g tablet prescription. He then started 4.8 grams of generic mesalamine tablets daily every morning. On day 1 of the generic mesalamine, while noting no therapeutic effect, he began to experience moderate costochondral chest pain that limited his range of motion and his ability to take a deep breath which worsened over the next 2 days. PA (posterior-anterior) and lateral chest X ray with rib views were normal. Mesalamine was discontinued with resolution of chest pain symptoms over the ensuing 5 days, but persistent colitis symptoms.

Lab work at that time revealed a mildly elevated white blood cell count of 11600/mm$^3$, mild anemia with hemoglobin 12.6 g/dL, markedly elevated ESR of 72 mm/hr and CRP of 45.4 mg/L. Iron saturation was low at 10%. Comprehensive metabolic panel was normal. Despite a dietary change eliminating all meat as well as turmeric capsule supplementation, colitis symptoms worsened with increased frequency, bleeding and pain. A stool sample was sent for a Diarrhea Pathogen Panel as well as Immunoassays for Diarrhea (Genesis Laboratory Management, LLC, Oakhurst, NJ). Pathogen panel was completely negative for 23 pathogens, ova and parasites. Immunoassays revealed elevated calprotectin 298.4 µg/g, lactoferrin 49.8 µg/mL and eosinophil-derived neurotoxin (EDN) of 7111.0 ng/ml (>1700 ng/ml is considered "Very high") consistent with an inflammatory diarrhea. At this point, the decision was made to start prednisone at a dose of 40 mg daily. After 7 days he noted no improvement of his symptoms. Due to concerns over the rapidly evolving COVID-19 pandemic at this time, the decision was made to rapidly taper off the prednisone over 3 days as it had not caused any improvement in symptoms. Labs were repeated. Hemoglobin dropped to 11.6 g/dL. CT scan of the abdomen and pelvis showed a markedly thickened colonic wall from the rectum to the splenic flexure consistent with a left sided colitis. Colonoscopy 4 days later revealed moderate to severe colitis marked by erythema, erosions, loss of vascular pattern and friability starting in the rectum and extending up into the distal transverse colon. Biopsies were consistent with a moderately active chronic colitis with lymphoplasmacytosis and gland architectural distortion. Rare crypt abscesses were noted but no granulomas or viral changes were seen. A diagnosis of ulcerative colitis was made.

Having failed conventional therapy with prednisone and mesalamine, as well as rifaximin and dietary/turmeric supplement therapy before that, and with the growing concern over the COVID-19 pandemic, the patient was extremely reluctant to begin infliximab (REMICADE®) or vedolizumab (ENTYVIO®) as recommended by his gastroenterologist. He recalled that on his recent 2 week trip to India 3 months prior, he had a remarkable lack of any GI symptoms with none of his prior "IBS" type symptoms. He also recalled that he was on the malaria prophylaxis agent atovaquone/proguanil adult dose once daily (250 mg atovaquone, 150 mg proguanil). He had about 15 tablets left from that prescription and began taking one daily. By day 3, he noted that his abdominal pain was gone. His stools began to decrease in frequency with more form and less blood. By day 10, he was asymptomatic and feeling well. He continues on the medication one month later reporting no side effects and no symptoms of colitis.

CONCLUSION

This case represents the first reported use of atovaquone for an inflammatory bowel disease or any disease or condition of inflammation. This could have implications for treating not just IBD, but other inflammation-mediated conditions such as metabolic syndrome, atherosclerosis, neurologic conditions, rheumatoid arthritis as well as many others.

What is claimed is:

1. A method of treating a disease or condition in a subject in need thereof, comprising administering to the subject an effective amount of atovaquone, or a salt thereof, wherein the disease or condition is selected from the group consisting of rheumatoid arthritis, systemic lupus erythematosus, type 1 diabetes, atopic dermatitis, asthma, chronic obstructive pulmonary disease, Alzheimer's disease, multiple sclerosis, obesity, hidradenitis suppurativa, pancreatitis, stroke, colorectal cancer, anti-phospholipid syndrome, non-alcoholic steatohepatitis, myocardial infarction, congestive heart failure, and psoriasis.

2. The method of claim 1, further comprising administering to the subject an effective amount of proguanil, or a salt thereof.

3. The method of claim 1, wherein the disease or condition is refractory to a therapy comprising: an anti-inflammatory agent, an immunosuppressant drug, a 5-aminosalicylate (5-ASA), a corticosteroid, a tumor necrosis factor (TNF)-alpha inhibitor, an alpha-4 integrin inhibitor, an IL-12 and IL-23 inhibitor, a biologic, a biosimilar, an antibiotic, a dietary supplement, a laxative, an antispasmodic, an antidepressant, anti-diarrheal medication, a pain medication, and/or a surgery.

4. The method of claim 1, wherein:
  (i) the atovaquone, or salt thereof, is administered at a dosage of between about 0.5 mg to about 4,000 mg, about 100 mg to about 3,000 mg, about 500 mg to about 2000 mg or at about 1000 mg; and/or
  (ii) the atovaquone, or salt thereof, is administered at a dosage of about 0.5 mg, about 1 mg, about 5 mg, about 10 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1,000 mg, about 1,250 mg, about 1,500 mg, about 1,750 mg, or about 2,000 mg, about 2,250 mg, about 2,500 mg, about 2,750 mg, about 3,000 mg, about 3,250 mg, about 3,500 mg, about 3,750 mg, about 4,000 mg of atovaquone, or a salt thereof.

5. The method of claim 2, wherein:
  (i) the proguanil, or salt thereof, is administered at a dosage of between about 0.5 mg to about 2,000 mg, about 50 mg to about 1500 mg, about 100 mg to about 1000 mg, or at about 400 mg; and/or
  (ii) the proguanil, or salt thereof, is administered at a dosage of about 0.5 mg, about 1 mg, about 5 mg, about 10 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1,000 mg, about 1,250 mg, about 1,500 mg, about 1,750 mg, or about 2,000 mg of proguanil, or a salt thereof.

6. The method of claim 4, wherein the dosage is a daily dosage.

7. The method of claim 2, wherein:
  (i) the atovaquone and/or proguanil is administered simultaneously, in the same or in separate compositions, or sequentially;
  (ii) the atovaquone and/or proguanil is administered orally, optionally, as a liquid or a tablet;
  (iii) the atovaquone and/or proguanil is administered at least every 6 hours, at least every 12 hours, at least once a day, or at least once every other day, optionally, wherein the composition is administered at least once a day (QD), at least twice a day (BID), at least three times a day (TID), or continuously; and/or
  (iv) the atovaquone and/or proguanil is administered for at least about 3 days to about 30 days, at least about 4 days to about 7 days, up to about 10 days, at least about 2 weeks, at least about 4 weeks, at least about 8 weeks, at least about 14 weeks, at least about 16 weeks, at least about 24 weeks, at least about 1 year, at least about 2 years, or the duration of the subject's life.

8. The method of claim 1, wherein the subject is human.

9. The method of claim 1, further comprising administering an additional therapy to the subject.

* * * * *